(12) United States Patent
Sjogren et al.

(10) Patent No.: US 9,463,221 B2
(45) Date of Patent: *Oct. 11, 2016

(54) STABILIZATION OF FSH

(71) Applicant: Ferring B.V., Hoofddorp (DK)

(72) Inventors: Helen Ulrika Sjogren, Lund (SE); Heidi Louise Bagger, Copenhagen S (DK)

(73) Assignee: Ferring B.V., Hoofddorp (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/631,382

(22) Filed: Feb. 25, 2015

(65) Prior Publication Data

US 2015/0265681 A1    Sep. 24, 2015

Related U.S. Application Data

(63) Continuation of application No. 13/704,771, filed as application No. PCT/EP2011/062986 on Jul. 28, 2011, now Pat. No. 8,993,732.

(30) Foreign Application Priority Data

Jul. 30, 2010 (EP) ..................... 10171428

(51) Int. Cl.
| | |
|---|---|
| *C07K 1/00* | (2006.01) |
| *C07K 14/00* | (2006.01) |
| *C07K 16/00* | (2006.01) |
| *C07K 17/00* | (2006.01) |
| *A61K 38/24* | (2006.01) |
| *A61K 9/00* | (2006.01) |
| *A61K 47/02* | (2006.01) |
| *A61K 47/12* | (2006.01) |
| *C07K 14/59* | (2006.01) |
| *A61K 47/10* | (2006.01) |

(52) U.S. Cl.
CPC ............ *A61K 38/24* (2013.01); *A61K 9/0019* (2013.01); *A61K 47/02* (2013.01); *A61K 47/10* (2013.01); *A61K 47/12* (2013.01); *C07K 14/59* (2013.01)

(58) Field of Classification Search
None
See application file for complete search history.

(56) References Cited

U.S. PATENT DOCUMENTS

| | | |
|---|---|---|
| 5,929,028 A | 7/1999 | Skrabanja et al. |
| 2008/0051329 A1 | 2/2008 | Hoffmann et al. |
| 2010/0324269 A1* | 12/2010 | Shultz .......... C07K 1/1133 530/387.1 |

FOREIGN PATENT DOCUMENTS

| | | | |
|---|---|---|---|
| EP | 0814841 | 1/1998 | |
| EP | 974359 | 12/2002 | |
| EP | 1285665 | 2/2003 | |
| WO | WO 2007/037607 | * 4/2007 | .............. A61K 9/08 |
| WO | WO 2009/127826 | 10/2009 | |
| WO | WO 2011/099036 | 8/2011 | |

OTHER PUBLICATIONS

European Pharmacopoeia 5.0, "2.2.35. Osmolality," 2005, p. 54.
Burton et al., "Use of microcalorimetly and its correlation with size exclusion chromatography for rapid screening of the physical stability of large pharmaceutical proteins in solution," Pharm. Dev. Technol., 2007, 12(3), 265-73.
Dias, et al., "Structural biology of human follitropin and its receptor," Arch. Med. Res., 2001, 32(6), 510-9.
Funk, "Protein aggregation: folding aggregates, inclusion bodies and amyloid," Fold. Des., 1998, 3(1): R9-R23.
Fox et al., "Three-dimensional structure of human follicle-stimulating hormone," Mol. Endocrinol., 2001, 15(3), 378-89.
Howles, "Genetic engineering of human FSH (Gonal-F)," Hum. Reprod. Update, 1996, 2(2), 172-91.
International Search Report dated Feb. 28, 2012, which issued in corresponding International Application Serial No. PCT/EP2011/062986.
Lam et al., "The effect of benzyl alcohol on recombinant human interferon-gamma," Pharm. Res., 1997, 14(6), 725-9.
Maa et al., "Aggregation of recombinant human growth hormone induced by phenolic compounds," International Journal of Pharmaceutics, 1996, 140(2), 155-168.
Pierce et al., "Glycoprotein hormones: structure and function," Ann. Rev. Biochem., 1981, 50, 465-95.
Rathnam et al., "Primary amino acid sequence of follicle-stimulating hormone from human pituitary glands. I. alpha subunit," J. Biol. Chem., 1975, 250(17), 6735-46.
Remmele et al., "Interleukin-1 receptor (IL-1R) liquid formulation development using differential scanning calorimetry," Pharm. Res., 1998, 15(2), 200-8.
Saxena et al., "Amino acid sequence of the beta subunit of follicle-stimulating hormone from human pituitary glands," J. Biol. Chem., 1976, 251(4), 993-1005.
Van Hell et al, "Effects of Human Menopausal Gonadotrophin Preparations in Different Bioassay Methods," Acta Endocrinol., 1964, 47, 409-418.
Zhang et al., "Mechanism for benzyl alcohol-induced aggregation of recombinant human interleukin-1 receptor antagonist in aqueous solution," J. Pharm. Sci., 2004, 93(12), 3076-89.

* cited by examiner

Primary Examiner — Shulamith H Shafer
(74) Attorney, Agent, or Firm — Fish & Richardson P.C.

(57) ABSTRACT

The present invention pertains in general to the field of stabilization of FSH formulations, in particular liquid FSH formulations. The stabilization is achieved by the addition of salts comprising pharmaceutically acceptable alkali metal cations, in preferred embodiments by the addition of pharmaceutically acceptable salts, i.e. sodium salts or potassium salts.

25 Claims, 6 Drawing Sheets

STABILIZATION OF FSH

CROSS-REFERENCE TO RELATED APPLICATIONS

This application is a continuation of U.S. application Ser. No. 13/704,771, which is the U.S. National Phase under 35 U.S.C. §371 of International Application No. PCT/EP2011/062986, which was filed internationally on Jul. 28, 2011, which claims the benefit of European Application 10171428.5, filed Jul. 30, 2010.

FIELD OF THE INVENTION

The present invention pertains in general to the field of stabilization of FSH formulations, in particular liquid FSH-formulations. The stabilization is achieved by the addition of salts, in preferred embodiments by the addition of salts with alkali metal cations of pharmaceutically acceptable salts, i.e. Na- or K-salts, or combinations thereof.

BACKGROUND

Gonadotropins are a family of hormones, which are essentially mainly involved in the fertility cycle in females and males. Gonadotropins can be derived from urine, both for research and treatment purposes, however several gonadotropins can be produced recombinantly.

In particular, gonadotropins can be employed in the treatment of infertility.

The four main gonadotropins which are involved here and which all belong to the same glycoprotein family are follicle stimulating hormone (FSH), thyroid stimulating hormone (TSH), luteinizing hormone (LH) and chorionic gonadotropin (hCG). All of these gonadotropins consist of an alpha and a beta subunit; the alpha subunit is common to all, i.e. the same for all above-mentioned four gonadotropins, while the beta subunit differs, respectively.

As mentioned above, the gonadotropins are a group of heterodimeric glycoprotein hormones which regulate gonadal function in the male and female. They include follicle stimulating hormone (FSH), luteinising hormone (LH), thyroid stimulating hormone (TSH) and (human) chorionic gonadotropin (hCG).

FSH is naturally secreted by the anterior pituitary gland and functions to support follicular development and ovulation. FSH comprises a 92 amino acid alpha subunit, also common to the other glycoprotein hormones, e.g. LH and hCG, and a 111 amino acid beta subunit unique to FSH that confers the biological specificity of the hormone (Pierce and Parsons, 1981, Glycoprotein hormones: structure and function, Ann Rev Biochem., 50: 465-495). Each subunit is post-translationally modified by the addition of complex carbohydrate residues. Both subunits carry two sites for N-linked glycan attachment, the alpha subunit at amino acids 52 and 78 and the beta subunit at amino acid residues 7 and 24 (Rathnam and Saxena, (1975) Primary amino acid sequence of follicle stimulating hormone from human pituitary glands. I. alpha subunit, J Biol Chem. 250 (17):6735-6746; Saxena and Rathnam, (1976) Amino acid sequence of the beta subunit of follicle-stimulating hormone from human pituitary glands, J Biol Chem. 251(4): 993-1005)). FSH is thus glycosylated to about 30% by mass (Dias and Van Roey, (2001) Structural biology of human follitropin and its receptor. Arch Med Res. 32(6): 510-519; Fox et al. (2001) Three-dimensional structure of human follicle-stimulating hormone. Mol Endocrinol. 15(3), 379-89).

FSH purified from post-menopausal human urine has been used for many years in infertility treatment; both to promote ovulation in natural reproduction and to provide oocytes for assisted reproduction technologies. Two recombinant versions of FSH, Gonal-f (Merck Serono) and Puregon (Schering-Plough) became available in the mid-1990s. These are both expressed in Chinese hamster ovary (CHO) cells (Howles, C. M. (1996), genetic engineering of human FSH (Gonal-f), Hum Reprod. Update, 2: 172-191). CG is frequently used in infertility treatments because of this compound having an LH activity.

Both human FSH and hCG are heterodimers composed of an alpha and a beta subunit. The alpha subunit in both hormones is identical. Differences between the two hormones are conferred by the beta subunit. The mature beta subunit of FSH is composed of 111 amino acids, while that of hCG is composed of 145 amino acids, additionally the primary amino acid sequence of the FSH and hCG beta subunit are differing throughout the whole beta chain. The beta chain of both FSH and hCG contains six disulfide bridges, due to their different amino acid sequence they do however differ in their higher order structure, resulting in a different folding and distribution of charged, polar and hydrophobic regions (Fox et al. (2001) Three-dimensional structure of human follicle-stimulating hormone. Mol Endocrinol. 15(3), 379-89).

Although both beta subunits of FSH and hCG are glycosylated, the beta subunit of FSH contains only N-glycosylation (N-7 and N-24) while the beta subunit of hCG contains both N- and O-glycosylation (N-13, N-30, O-121, O-127, O-132 and O-138). The extra glycosylation in the beta subunit of hCG makes it more hydrophilic than that of FSH. β-subunits provide specificity for the receptor interaction.

CHO cells are commonly used for the production of pharmaceutical recombinant proteins. Structural analysis has identified that sialic acid is exclusively attached by an α2,3-linkage. Many human glycoproteins contain a mixture of both α2,3- and α2,6-linkages for sialic acid residues. Therefore, recombinant proteins expressed using the CHO system will differ from their natural counterparts in their type of terminal sialic acid linkages.

Infertility

In the present context, "infertility" shall be defined as the diminished ability or the inability to conceive and have offspring. Women who are able to get pregnant but then have repeat miscarriages are also said to be infertile. Infertility is also defined in specific terms as the failure to conceive after a year of regular intercourse without contraception. Infertility can be due to many causes. Studies have shown that a little more than half of cases of infertility are a result of female conditions. The remainder are caused by sperm disorders and by unexplained factors.

There are currently several possibilities to treat infertility. Those are a timed intercourse, the use of assisted reproductive technologies (ARTs), a medical management of endometriosis, fibroids and female sexual dysfunction (FSD), and surgery to correct abnormalities.

In assisted reproductive technology, drugs to stimulate ovulation are used. Next to LH and hCG, FSH is one of those compounds which is used in this context.

For administration, liquid formulations of these compounds are suitable. Unfortunately, it has been shown in the past that the preservatives added to liquid formulations, in particular benzyl alcohol (BA), phenol and m-cresol, exert a destabilizing effect on the protein (Maa, Y. F. and Chung, C. H. 1996, Aggregation of recombinant human growth hormone induced by phenolic compounds. *Int. J. Pharm.* 140: 155-168; Lam, X. M., Patapoff, T. W., and Nguyen, T. H. 1997, The effect of benzyl alcohol on recombinant human interferon-gamma. *Pharm. Res.* 14:725-729; Hoffmann, J. A. and Lu, J. 2002, FSH and FSH variant formulations comprising benzyl alcohol as a preservative. EP0974359B1, 1-50).

It is therefore important to provide a stabilized formulation, in particular in view of the fact that the dosage of the FSH to be administered should reduce the risk of side effects of dissociated or aggregated forms like immunogenic responses, if non-native FSH is present. The destabilizing events resulting from preservatives however decrease the actual level of active gonadotropin, i.e. FSH, within a liquid formulation.

Thus, it is an aim of the present invention to provide formulations, in particular liquid formulations of FSH, which are stable, as well as a method for their stabilization.

SUMMARY OF THE INVENTION

The present invention pertains to the use of salts comprising pharmaceutically acceptable alkali metal cations for the stabilization of a liquid FSH formulation so as to stabilize a liquid FSH formulation. The liquid formulation to be stabilized can be a formulation with or without preservative.

The following embodiments are preferred:

1. Use of salts comprising pharmaceutically acceptable alkali metal cations for the stabilization of a liquid FSH formulation, wherein the salt is selected from the group consisting of pharmaceutically acceptable $Na^+$-salts and $K^+$-salts, or a combination thereof.

2. Use according to item 1, wherein the salts are $Na^+$-salts.

3. Use according to any of items 1 or 2, wherein the salt is NaCl or $Na_2SO_4$.

4. Use according to any of items 1 or 2, wherein the salt is $Na_2SO_4$.

5. Use according to any of items 1 or 2, wherein the salt is a combination of NaCl and $Na_2SO_4$.

6. Use according to any one of items 1 to 5 wherein the salt is comprised in an amount of 20 to 500 mM, or in an amount of 30-300 mM or in an amount of 50-200 mM.

7. Use according to any one of items 1 to 6 wherein the FSH formulation is an rFSH formulation.

8. Use according to any one of items 1 to 7 wherein the formulation additionally comprises a preservative.

9. Use according to item 8 wherein the formulation comprises benzyl alcohol, phenol and/or m-cresol.

10. Use according to any one of items 1-9, wherein the formulation is an injectable formulation.

11. Method for stabilization of a liquid FSH formulation wherein the method comprises the step of an addition of salts comprising pharmaceutically acceptable alkali metal cations to said formulation, wherein said salts are selected from the group consisting of $Na^+$-salts and $K^+$-salts or a combination thereof.

12. Method according to item 11 wherein the salts are defined as in items 2 to 6 above.

13. Method according to items 11 and/or 12 wherein the FSH to be stabilized is rFSH.

14. Method according to any one of items 11 to 13 wherein the formulation additionally comprises a preservative.

15. Method according to item 14 wherein the preservative is selected from the group consisting of benzyl alcohol, phenol and m-cresol.

16. Use according to any one of items 1-10, wherein the liquid formulation is a re-constituted liquid formulation, which has been obtained from a freeze-dried formulation.

17. The method of any one of items 11-15, wherein the step of adding the salt is conducted before a freeze-drying step.

18. The method of item 17, wherein a re-constitution step is carried out after the freeze-drying step.

19. The method of item 17 and/or 18 wherein the salt is comprised in the freeze dried formulation or wherein the salt is comprised in a re-constitution liquid.

The formulation which has been supplied with the stabilizing salt is thus in an alternative embodiment stored in a freeze-dried state. Freeze-drying is carried out as generally known to a person skilled in the art. The freeze-dried formulation can then be stored until final use with the patient. Before administration, the freeze-dried formulation is then re-constituted with any one of the known reconstitution media, e.g. sterilized water. The salt is either comprised in the freeze-dried formulation or in the re-constitution liquid.

20. Use or method of any of the above items wherein the liquid formulation is a single use formulation or a multi-dose formulation, preferably for injection.

In a preferred embodiment, the salt is comprised in the liquid formulation per se which is not freeze-dried but kept as a liquid in storage.

In particular, in a preferred embodiment, the present invention pertains to the stabilization of a liquid FSH formulation wherein the alkali metal cation is selected from the group consisting of $Na^+$ and $K^+$. Particularly preferred, the salt is NaCl or $Na_2SO_4$.

As described above, liquid FSH formulations are suitable for the treatment of infertility. In that regard, it has become clear that liquid FSH formulations can be unstable; this is true for all liquid FSH formulations including those destined for single use. Instability can be even more pronounced if the liquid FSH formulations comprise a preservative, which is e.g. necessary for all multidose formulations. This preservative can be every preservative useful for preserving an FSH formulation; thus, the preservative could be a preservative as approved by the FDA for FSH formulations, in particular e.g. an FDA approved preservative, approved for parenteral FSH formulations, like for example benzyl alcohol, phenol and/or m-cresol; the preservative is however by no means limited to those examples. The stability of FSH is decreased e.g. by benzyl alcohol, phenol and/or m-cresol.

Accordingly, the presently claimed and described salts comprising pharmaceutically acceptable cations, are used for the stabilization of single-use FSH formulations.

Furthermore, the presently claimed and described salts comprising pharmaceutically acceptable cations, are used for the stabilization of multi-dose FSH formulations; such formulations need not comprise a preservative but may also comprise a preservative.

The addition of the presently claimed salts comprising pharmaceutically acceptable cations, i.e. $Na^+$- and $K^+$-salts, stabilizes a liquid FSH formulation. In a particularly preferred embodiment, the salts are pharmaceutically acceptable salts. Stabilization is achieved in single use or multi-dose formulations, in particular over a longer period of storage and can in a further possible embodiment be advantageous as a countermeasure to the destabilizing effect of preservatives, like benzyl alcohol, phenol and/or m-cresol.

The salts, which can be used according to the present invention, include, in a preferred embodiment NaCl or $Na_2SO_4$.

The salt is preferably comprised in an amount of 20 to 500 mM, even more preferably it is comprised in an amount of 30-300 mM; in a particular preferred embodiment it is comprised in an amount of 50-200 mM.

The maximum amount of salt added is limited to the solution osmolality. To minimise pain upon injection, the solution should preferably be isotonic or at least not hypertonic. Since all excipients in the solution contribute to the osmolality, the maximum amount of salt that could be added to a solution is dependent of the amount of other present components.

The salt is preferably comprised in a amount resulting in a maximum osmolality of 350 mosmol/kg, even more preferably in an amount resulting in a maximum osmolality of 320 mosmol/kg; in a particular preferred embodiment it is comprised in an amount resulting in a maximum osmolality of 300 mosmol/kg.

Osmolality Theory

Osmolality is a practical means of giving an overall measure of the contribution of the various solutes present in a solution to the osmotic pressure of the solution. The osmolality can be measured in accordance with the Ph. Eur. 2.2.35, $7^{th}$ edition, supplement 2011 (7.2), Osmolality, January 2008:20235.

A "salt" in the context of the present invention is a chemical compound derived from an acid by replacing hydrogen, wholly or partly, with a metal or an electropositive radical.

The definition of "salts with (or comprising) cations of pharmaceutically acceptable salts" refers to all those salts which are formed with cations which are approved for i.m. or s.c. delivery according to the FDA inactive ingredients list; the alkali metal cations of this group are sodium ($Na^+$) and potassium ($K^+$).

The inventors have surprisingly found that two very specific cations are particularly suitable for the stabilization of an FSH formulation.

The salts could thus be formed with the following pharmaceutically acceptable cations: potassium (mono-, di- or tribasic), or sodium (mono- or di- or tri-basic). Preferably, the salts are sodium-salts.

Particularly preferred are NaCl and $Na_2SO_4$.

The gonadotropin which can be stabilized according to the present invention is FSH, i.e. follicle stimulating hormone, optional in combination with further active ingredients.

The FSH is urinary or plasma-derived or recombinant FSH (rFSH). In a preferred embodiment, the FSH is urinary or rFSH; particularly preferred it is rFSH.

As mentioned above, it is now possible to produce FSH recombinantly. Thus, reference here to an FSH in general always includes both the urinary derived as well as the recombinant (r) gonadotropin. Thus, reference to FSH also encompasses rFSH.

In a preferred embodiment of the invention, the formulation is a liquid rFSH formulation, most preferably injectable, which is stabilized by $Na_2SO_4$ or NaCl.

In a preferred embodiment of the invention, the formulation is a liquid rFSH formulation, most preferably injectable, which is stabilized by $Na_2SO_4$ or NaCl.

In an alternative embodiment, the rFSH of all embodiments is a long-acting FSH. The long-acting FSH formulations can be obtained as generally known to a person skilled in the art, e.g. by modifying the FSH molecule or by modifying the formulation.

FSH here thus encompasses all possible urinary derived or recombinant forms of the above-mentioned FSH as well as all possible combinations of FSH forms. Also encompassed is a formulation for single use and one or more further formulations (of the same or a different gonadotropin) for multi-dose use.

One possible product may be a formulation including FSH (optionally with CG, LH, LH activity etc.), all in different vials. The LH activity, if present, may originate from LH or CG. LH can be replaced by an equivalent dose of CG and vice versa; an "equivalent dose" in that context can be calculated on the basis that 1 IU of CG is equivalent to 5-7 IU of LH in the Pharmacopeia Van Hell Bioassay (Van Hell, H et al, Acta Endocrin. 47, 409-418, 1964).

A preferred combination is that of (r)FSH, (r)LH and (r)hCG, all in different vials.

Possible combinations in different vials also include: urinary (u) FSH and uhCG or uFSH and uLH; further (rhCG or rLH or rFSH) and (uhCG or uLH or rhCG or rLH), and all possible permutations thereof.

Another preferred combination is that of (r)FSH and (r)hCG, in different vials, respectively.

Another preferred combination is that of (r)FSH and (r)LH, in different vials, respectively.

The FSH formulation of the present invention is a liquid formulation. Preferably, the formulation is injectable.

Formulations can be supplied as a product having one, two or more pharmaceutical composition(s) including FSH or FSH/hCG, for administration separately or together. If administered separately, administration can be sequential. The product can be supplied in any appropriate package. For example, a product can contain a number of pre-filled syringes each including FSH (an FSH composition), or additionally hCG (an hCG composition) e.g. wherein the syringes can be packaged in a blister package or other means to maintain sterility. A product can optionally contain instructions for using the FSH formulations.

According to a further aspect, the inventive FSH formulation is provided as a multi-dose preparation. The present invention, however, explicitly is also directed to formulations destined for a single use. The present invention also pertains to a stabilization of formulations as part of a kit. Such a kit will comprise at least one container comprising one or more daily doses of FSH, or e.g. two containers (e.g. a vial), each comprising a different gonadotropin, and e.g. further instructions (e.g. for administration) and e.g. further means for injection. In a preferred embodiment, an injection pen for multiple injections is used, whereby the FSH solution is filled in respective cartridges.

In a preferred embodiment, the FSH is comprised with 35-850 IU/ml, preferably 50-800 IU/ml, even more preferred 100-600 IU/ml.

A particularly preferred formulation for e.g. 600 IU/ml rFSH has the following composition:
  600 IU/ml rFSH
  0.001-0.05, preferably 0.005 mg/ml Polysorbate 20
  0.1 to 10, preferably 1.0 mg/ml L-methionine
  0.5 to 50, preferably 5.0 mg/ml phenol
  1 to 100, preferably 14 mg/ml disodium sulphate (i.e. 0.1 M)
  0.1 to 10, preferably 1 mM sodium phosphate buffer, (pH 6 to
  8, preferably pH 6.5).
The solution osmolality is preferably 300 mosmol/kg
  (The pH refers to the pH of the whole solution.)
  Injectable depot forms can be made by forming microencapsule matrices of FSH (and other agents, if present) in biodegradable polymers. The polymer based depot forms/sustained release systems can, dependent on their chemical nature, be for example micro- or nano particles, hydrogels, micelles, emulsions or implants. Depending upon the ratio of FSH to polymer and the nature of the particular polymer employed, the rate of FSH release can be controlled. Examples of biodegradable polymers include polylactide/ polyglycolide copolymer systems, polyvinylpyrrolidone, poly(orthoesters), poly(anhydrides), poly(ethylene glycol), poly amino acids, polysaccharides e.g. sodium hyaluronate (NaHA) or other slats hereof, gelatine, chitosan etc. All mentioned polymers can be derivatized or modified to optimize the protein drug delivery or its stability. Depot injectable formulations are also prepared by entrapping the FSH in lipid systems, or polymer lipid mixtures as micelles, liposomes or microemulsions which are compatible with body tissues.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like, as described above.

The pH and exact concentration of the various components of the pharmaceutical composition are adjusted in accordance with routine practice in this field. See GOODMAN and GILMAN's THE PHARMACOLOGICAL BASIS FOR THERAPEUTICES, 7th edition. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

The FSH of the present invention can be derived by conventional means from urine or can be produced recombinantly. For possible production methods it is further referred to e.g. WO 2009/127826.

hCG can be obtained by any means known in the art. hCG as used herein includes human-derived and recombinant hCG. Human-derived hCG can be purified from any appropriate source (e.g. urine and placenta) by any method known in the art. Methods of expressing and purifying recombinant hCG are well known in the art.

LH can be obtained by any means known in the art. LH, as used herein, includes human-derived and recombinant LH. Human-derived LH can be purified from any appropriate source (e.g. urine) by any method known in the art. Methods of expressing and purifying recombinant LH are known in the art.

The pharmaceutical composition may be for the treatment of infertility, e.g. for use in e.g. assisted reproductive technologies (ARTs), ovulation induction (OI) or intrauterine insemination (IUI). The pharmaceutical composition may be used, for example, in medical indications where known FSH preparations are used. The present invention also provides the use of the stabilized FSH preparation described herein (according to aspects of the invention) for, or in the manufacture of a medicament for, the treatment of infertility. The pharmaceutical compositions can be formulated into well-known compositions for any route of drug administration, e.g. oral, rectal, parenteral, transdermal (e.g. patch technology), intravenous, intramuscular, subcutaneous, intracisternal, intravaginal, intraperitoneal, local (powders, ointments or drops) or as a buccal or nasal spray. A typical composition comprises a pharmaceutically acceptable carrier, such as aqueous solution, non-toxic excipients, including salts and preservatives, buffers and the like, as described in Remington's Pharmaceutical Sciences fifteenth edition (Matt Publishing Company, 1975), at pages 1405 to 1412 and 1461 to 87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxy-methylcellulose and suitable mixtures thereof, vegetable oils (such as olive oil), and injectable organic esters such as ethyl oleate.

The compositions can also contain additives such as but not limited to preservatives, wetting agents, emulsifying agents, buffering agents, and dispersing agents. Antibacterial and antifungal agents can be included to prevent growth of microbes and includes, for example, parabens, chlorobutanol, phenols, sorbic acid, and the like. Furthermore, it may be desirable to include tonicity agents.

In some cases, to effect prolonged action it is desirable to slow the absorption of FSH (and other active ingredients, if present) from subcutaneous or intramuscular injection. This can be accomplished by the use of a liquid suspension of crystalline or amorphous material with poor water solubility. The rate of absorption of e.g. FSH then depends upon its rate of dissolution which, in turn, can depend upon crystal size and crystalline form. Alternatively, delayed absorption of a parenterally administered FSH combination form is accomplished by dissolving or suspending the FSH combination in an oil vehicle.

According to the present invention, an effort was made by the inventors to investigate the effect of certain compounds on the stability of a liquid gonadotropin formulation; here, stabilizing as well as destabilizing effects of certain compounds were investigated.

The term "stability" can refer to chemical stability, involving covalent modification in the amino acid sequence, but in the context of protein stability it can also refer to physical stability, which involves changes of the protein folded state (i.e. the native state) not including covalent bond cleavage.

In the present invention the term "stability" refers to the physical, stability of formulations of gonadotropins, in particular FSH of the present invention. Physical instability of a protein formulation may be caused by aggregation of the protein molecules to form higher order aggregates, by dissociation of the heterodimers into monomers, or by any other conformational change that reduces at least one biological activity of FSH proteins included in the present invention.

A "stable" solution or formulation is one wherein the degree of, aggregation, dissociation, conformational modification, loss of biological activity and the like, of proteins therein is acceptably controlled, and does not increase unacceptably with time. Stability may be assessed by methods well-known in the art, including measurement of a sample's light scattering, visual inspection of clarity and/or coloration, absorbance, or optical density, molecular size determinations (e.g. by size exclusion chromatography or field flow fractionation), in vitro or in vivo biological activity and/or by differential scanning calorimetry (DSC).

Other methods for assessing stability are well known in the art and can also be used according to the present invention.

It was known that several preservatives have a pronounced destabilizing effect on gonadotropin formulations and it was found surprisingly here that salts, in particular salts comprising pharmaceutically acceptable alkali metal cations, which have been shown here to be suitable for the stabilization of a liquid FSH formulation, in particular $Na^+$ or $K^+$, such as NaCl or $Na_2SO_4$ are additionally useful to counteract the destabilizing effects of a preservative, like benzyl alcohol, phenol and m-cresol, which need to be comprised in a liquid multidose FSH formulation for medical use. The presently claimed salts have a stabilizing effect on a liquid FSH formulation which is in an advantageous and surprising manner even more pronounced than the stabilizing effects of known stabilizers, like e.g. sucrose. The improved stabilization effect compared to the known stabilizers like sucrose is particularly surprising. Further, quite unexpected, the stabilizing effects of the inventive salts could be shown for FSH formulations, although no stabilizing effect could be shown for the very similar hCG. It was further surprising that the stability effects as observed did not obey the so-called Hofmeister series (see also below), but actually ran against it.

It has been known from the prior art that there is degradation of FSH occurring in pharmaceutical FSH formulations and this has been confirmed by the first set of the present examples.

FSH will degrade both as a function of time as well as a function of temperature. In particular, at temperatures above room temperature, the secondary, tertiary and quaternary structures will be altered.

It appears that the conformational unfolding of tertiary and secondary FSH structures occurring upon heating is a two-state transition (when protein aggregation is limited). This unfolding may be independent on subunit dissociation (changes in the quaternary structure).

Further, it becomes clear with the present invention that FSH, containing a preservative like benzyl alcohol or phenol, where such preservatives are necessary, for example as antimicrobial agents in liquid FSH formulations, clearly affect the stability of FSH multidose formulations in a negative manner. Here, the long term stability of FSH is decreased, the denaturation temperature of FSH is lower, and the already denatured forms have a lower level of secondary structures than FSH formulations not containing preservatives.

The present invention also shows for the first time that salts comprising pharmaceutically acceptable alkali metal cations for the stabilization of a liquid FSH formulation, namely Na and K, have a significant effect on the stability of liquid FSH formulations. It could be shown that the secondary structure of FSH in liquid FSH formulations comprising these salts will not change significantly upon heating to 76.5° C. The denatured form is relatively structured in the presence of e.g. $Na_2SO_4$, this makes denaturation more reversible, and thus, significantly increase the kinetic stability of the protein. This is supported by the presently shown real time stability data showing a pronounced stabilizing effect on the heterodimeric structure of FSH.

The results here clearly indicate that the presently claimed salts, e.g. sodium sulphate and sodium chloride, can limit the tendency of FSH molecules to dissociate and thus significantly increase the storage stability.

The present invention also pertains to a method for stabilization of a liquid FSH formulation wherein the method comprises the step of an addition of the above salts to said formulation.

All studies were confirmed by the additionally conducted real-time data.

Figure 1:
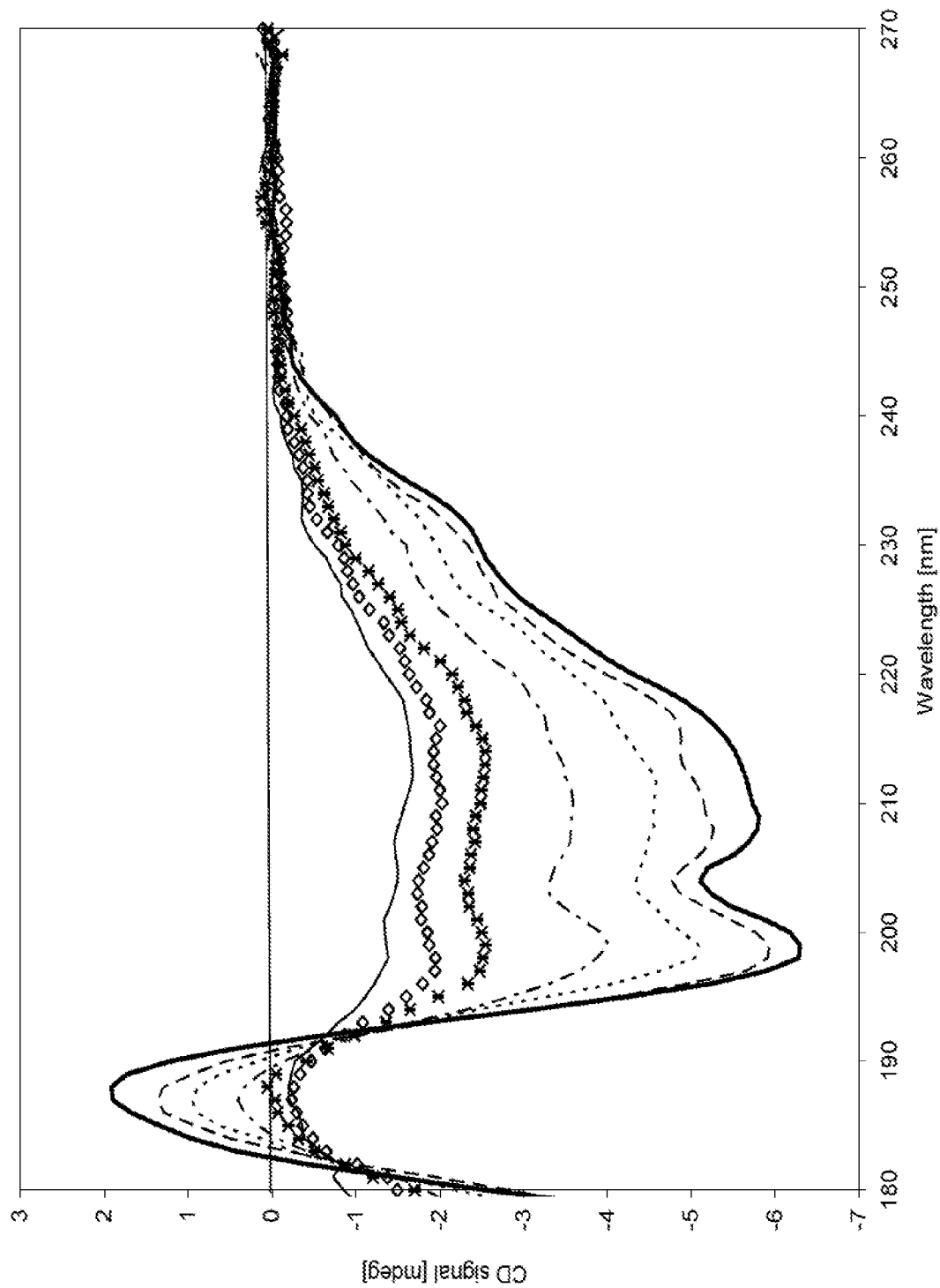
FIG. 1.

The CD (circular dichroism, see below) signal (mdegree) as function of wavelength (nm) is shown for rFSH at various temperatures. No significant difference between the 24.0° C.→45.9° C. spectra was observed but a temperature-dependent decrease of the CD-signal beyond 50° C. was observed. The rFSH protein (0.93 mg/ml) was dissolved in 3.57 mM phosphate buffer pH 6.3 containing 0.0036 mg/ml Polysorbate 20. Scan at 24.0° C. (bold solid trace), 50.3° C. (dashed trace), 54.7° C. (dotted trace), 59.0° C. (dashed-dotted trace), 63.4° C. (stars), 67.8° C. (diamonds) and 76.5° C. (solid trace).

FIG. 2:

The CD signal (mdegree) as a function of wavelength (nm) is shown for rFSH containing $Na_2SO_4$ at various temperatures. No significant difference between the 24.0° C.→45.9° C. spectra was observed. The rFSH protein was dissolved in 3.57 mM phosphate buffer pH 6.3 containing 0.0036 mg/ml Polysorbate 20 and 8.6 mg/ml sodium sulphate ($Na_2SO_4$). Scan at 24.0° C. (bold solid trace), 50.3° C. (dashed trace), 54.7° C. (dotted trace), 59.0° C. (dashed-dotted trace) and 76.5° C. (solid trace).

FIG. 3:

The CD signal (mdegree) as a function of wavelength (nm) is shown for rFSH containing benzyl alcohol at various temperatures. No significant difference between the 24.0° C.→45.9° C. spectra was observed. The rFSH protein (0.93 mg/ml) was dissolved in 3.57 mM phosphate buffer pH 6.3 containing 0.0036 mg/ml Polysorbate 20 and 0.17 mg/ml benzyl alcohol. Scan at 24.0° C. (bold solid trace), 45.9° C. (circles), 50.3° C. (dashed trace), 54.7° C. (dotted trace), 59.0° C. (dashed-dotted trace), 63.4° C. (stars), 67.8° C. (diamonds) and 76.5° C. (solid trace).

FIG. 4:

Subsequent DSC scans of hCG and rFSH. DSC data for 5 mg/ml hCG in 0.005 mg/ml Polysorbate 20, 0.5 mg/ml L-methionine, 1 mM phosphate buffer, pH 6.5 and 2.4 mg/ml rFSH in 0.005 mg/ml Polysorbate 20, 0.5 mg/ml L-methionine, 0.24 M NaCl, 1 mM phosphate buffer, pH 6.5. Scan rate 2.0° C./min. First rFSH scan (solid trace), second rFSH scan (dashed-dotted trace), first hCG scan (dashed trace) and second hCG scan (dotted trace). After the first scan the sample was cooled to 20° C. before the second scan.

FIG. 5:

DSC scans of hCG with various sugar or salts. DSC data for 5 mg/ml hCG in 0.005 mg/ml Polysorbate 20, 0.5 mg/ml L-methionine and 1 mM phosphate buffer, pH 6.5. No added sugar or salt (bold solid trace), 0.1 M $Na_2SO_4$ (solid trace), 0.1 M NaCl (dotted trace), 0.1 M $NaClO_4$ (dashed trace) and 0.1 M sucrose (dashed-dotted trace). Scan rate 2.0° C./min.

FIG. 6:

DSC scans of rFSH with various sugar and salts. DSC data for 2.4 mg/ml rFSH in 0.005 mg/ml Polysorbate 20, 0.5 mg/ml L-methionine and 1 mM phosphate buffer, pH 6.5. No added sugar or salt (bold solid trace), 0.1 M $Na_2SO_4$ (solid trace), 0.1 M NaCl (dotted trace), 0.1 M NaClO$_4$ (dashed trace) and 0.1 M sucrose (dashed-dotted trace). Scan rate 1.0° C./min.

The present invention is further explained by way of the following examples, which shall, however, by no means be construed to be limiting the scope thereof.

EXAMPLES

Example 1

Synchrotron Radiation Circular Dichroism Spectroscopy (SRCD)

Method

Circular Dichroism spectroscopy was performed by using a synchrotron facility at University of Aarhus, Denmark. All CD spectra was recorded using a 0.1 mm path length quartz suprasil cell (Hellma GmbH, Germany) over a wavelength range of 180-270 nm in 1 nm steps, and with a dwell time of 3 seconds per wavelength. Three identical CD scans were recorded for each experimental trial both for rFSH and reference (placebo) trials. The CD spectrum of rFSH presented in this report was obtained by subtracting the average corresponding placebo scan from the average protein scan. For each set of CD scans approximately 120 µl solution (corresponds to approximately 112 µg rFSH) was used.

During investigations of temperature effects on the rFSH CD spectrum, the temperature in the heating chamber was varied from 25° C. to 85° C. with 5° C.-intervals, and an equilibration time of 5 minutes. From a calibration file the actual experimental temperature (temperature in the quartz suprasil cell) was determined.

CD measures the difference in absorption of left- and right-handed circularly polarized light which occurs due to structural asymmetry. Secondary structures of proteins can be investigated by CD spectroscopy in the far UV region (approximately 180-250 nm). In general, more ordered structure follows more intense CD signals (positive or negative). However, different secondary structures have different CD spectra, and as α-helices have more intense CD signals than β-structures, no direct comparisons can be performed between different proteins to be concluded on the degree of ordered structures.

Due to the high sensitivity towards structural changes, CD spectroscopy is a strong tool when investigating physical stability of proteins. Such studies are usually performed by detecting a CD spectrum as function of changes in external factors e.g. temperature, pH, concentration of denaturants, surfactants or stabilizers. In the present study the CD spectrum of rFSH is investigated as function of temperature. Additionally the effects of benzyl alcohol and sodium sulphate (Na$_2$SO$_4$) on the rFSH secondary structure have been studied.

The gonadotropin used in this example as well as in Examples 2 and 3 is a recombinant Follicle Stimulating Hormone (rFSH), a human hormone which is expressed from the human PER.C6® cell line using recombinant DNA technology. rFSH is a heterodimer protein consisting of two glycosylated monomers: a 92 amino acid alpha-subunit which is common for FSH, Luteinizing Hormone (LH), Human Chorionic Gonadotropin (hCG) and Thyroid Stimulation Hormone (TSH), and a 111 amino acid beta-subunit which is specific for FSH. The glycoprotein hormones, comprising FSH, all loose their bioactivity upon dissociation of the non-covalently coupled monomers. Previous results have indicated that instability of rFSH is primarily based on dimer dissociation (decomposition of quaternary structure, and concomitant decrease in immunobinding response).

Dependent on the intended use, currently marketed rFSH formulations are provided in different concentrations, ranging from 37.5 IU/ml (corresponding to approximately 2.8 µg/ml for Gonal-f) up to at least 833 IU/ml (corresponding to approximately 83.3 µg/ml for Puregon).

The rFSH used in the studies is intended for a liquid drug product formulation, 600 IU rFSH/ml for subcutaneous injection. Since the product is aimed for multi-dose injection, addition of a preservative is of necessity.

The investigated formulations were produced by mixing stock solutions of the different ingredients. The investigated concentration interval of both the protein and the excipients is limited due to the method used, i.e. the protein concentration needed to be kept relatively high in comparison to the excipient concentrations. Due to UV absorption of aromatic compounds in the investigated wavelength region, the benzyl alcohol concentration needed to be kept low. The table below outlines the three different formulations that have been examined in a first experimental design by the present inventors.

TABLE 1

The table shows the content of the three formulations which were used for SRCD studies of the effects of temperature on rFSH

| Sample | Content |
|---|---|
| 1 | rFSH 0.93 mg/ml, Polysorbate 20 3.6 µg/ml, 3.57 mM Phosphate buffer pH 6.3 |
| 2 | rFSH 0.93 mg/ml, Polysorbate 20 3.6 µg/ml, Na$_2$SO$_4$, 8.6 mg/ml, 3.57 mM Phosphate buffer pH 6.3 |
| 3 | rFSH 0.93 mg/ml, Polysorbate 20 3.6 µg/ml, benzyl alcohol 0.17 mg/ml, 3.57 mM Phosphate buffer pH 6.3 |

The table shows the content of the three formulations which were used for SRCD studies of the effects of temperature on rFSH Sample 1

The CD spectrum was recorded for rFSH, sample 1 (see table 1) at thirteen different temperatures between 24° C. and 77° C. For clarity only seven of these spectra are shown in FIG. 1. Sample 1, as derivable from Table 1, comprised neither a salt, nor a preservative. The spectra are shown in FIG. 1. The results clearly show that the intensity of the CD signal decreases as a function of temperature, indicating the decomposition of secondary structures at high temperature (>50° C.). No significant differences between the 24.0° C.→45.9° C. spectra were detected, which shows that during the time period of the measurements (about 20 minutes) the secondary structure of the protein is intact upon heating to approximately 46° C. The SRCD spectra of FSH upon heating show an isodichroic point at approximately 193 nm, which is also found for the spectra of Sample 2, see FIG. 2.

Sample 2

Figure 2:
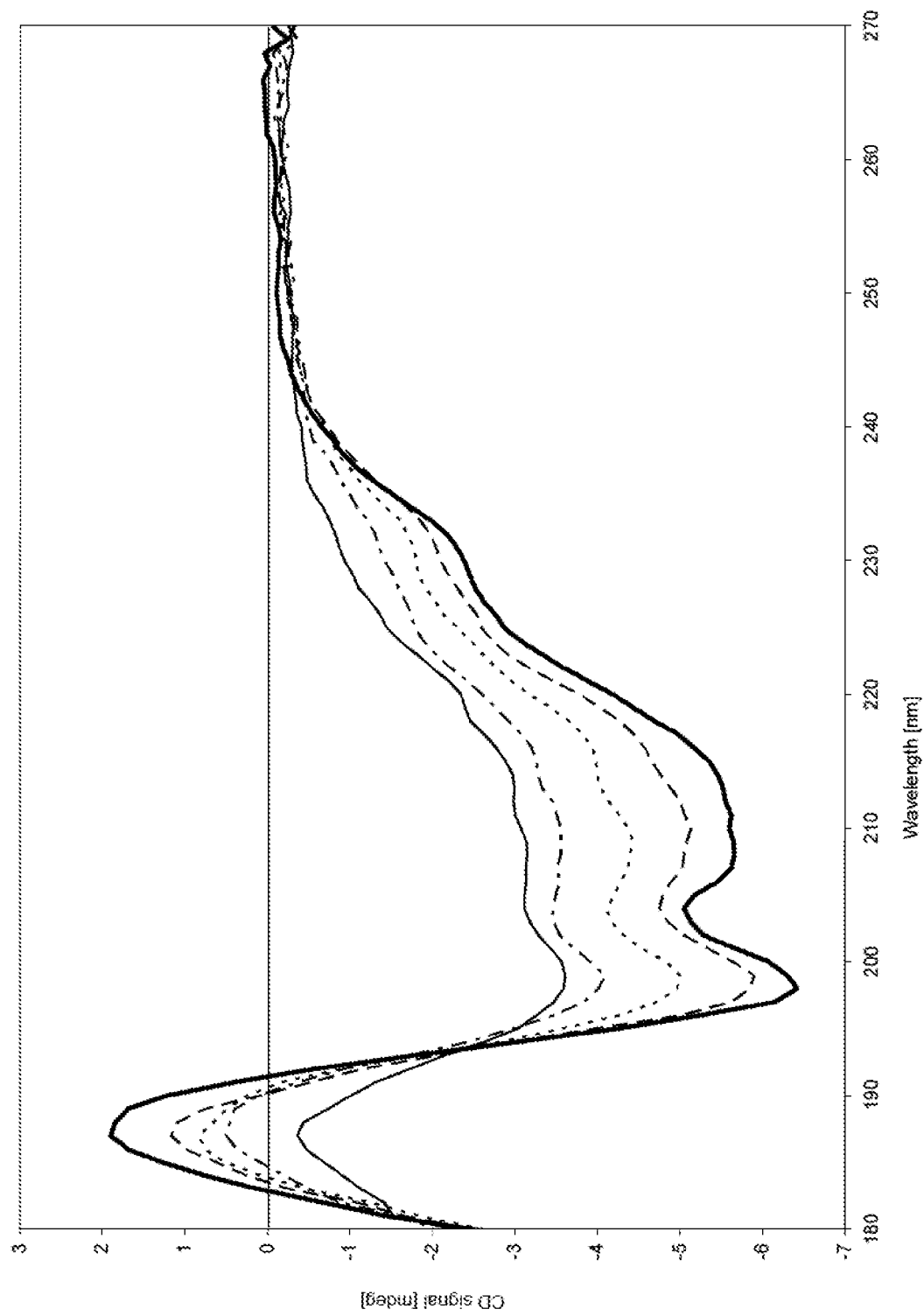

The CD spectrum was recorded for rFSH, sample 2 (table 1) containing Na$_2$SO$_4$. The spectra are obtained at thirteen different temperatures between 24° C. and 77° C., and presented in FIG. 2. For clarity only five of these spectra are shown in FIG. 2. The results show the decomposition of secondary structures as a function of temperature. The data reveals that the secondary structure of rFSH in sample 2 is intact upon heating to approximately 46° C. (in the duration of the experiment). Importantly, the data also shows that the denatured form is relatively structured in the presence of Na$_2$SO$_4$.

Sample 3

The CD spectrum was recorded for rFSH, sample 3 (table 1) containing benzyl alcohol (BA). Benzyl alcohol is an antimicrobial preservative which quite commonly is selected for a liquid formulation of FSH. Due to the relative weak preservation capacity compared to for example m-cresol, BA has to be used at high concentrations (about 10-15 mg/ml). A preservative is necessary since the intended use of rFSH is for several injections over a time period up to 1 month, and as rFSH is commonly stored at room temperature.

Figure 3:
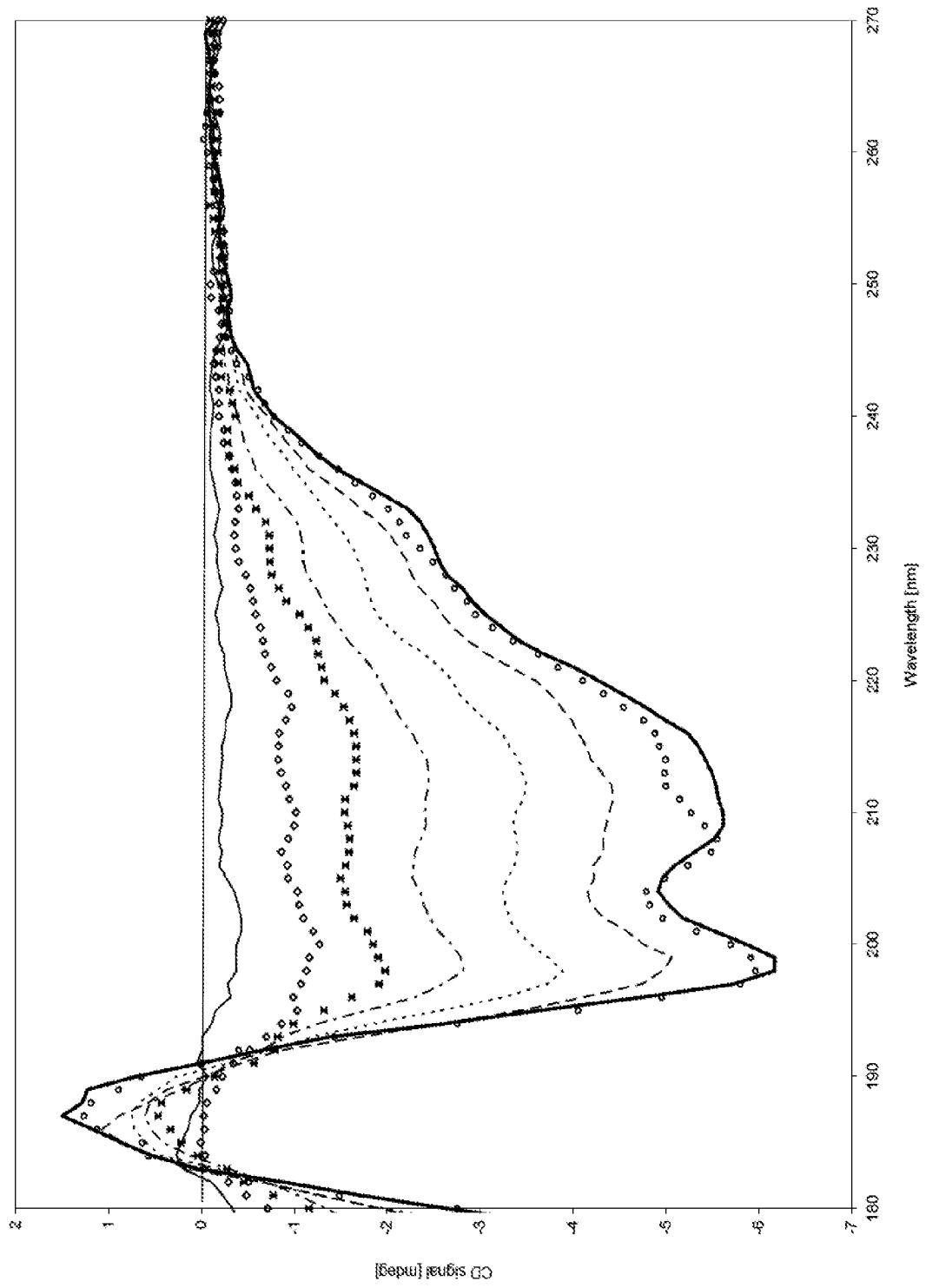

The spectra of rFSH in the presence of 0.17 mg/ml BA are obtained at thirteen different temperatures between 24° C. and 77° C., and presented in FIG. 3. For clarity only eight of these spectra are shown in FIG. 3.

Due to the very high UV absorbance of benzyl alcohol (and concomitant low CD signal) the investigated BA concentration could not be increased, and thus could not get even close to the concentration which will be used to preserve rFSH formulations. Nevertheless, a clear destabilizing effect of BA was observed. The CD results indicate that the secondary structure of rFSH in sample 3 is intact upon heating to 42° C., which is slightly lower than the onset denaturation temperature of rFSH in samples 1 and 2. Additionally, and importantly, the data shows that the denatured forms lack ordered structure to a markedly higher degree than FSH in the absence of preservative.

The Effects of Excipients on Temperature Induced Structural Changes

The salt $Na_2SO_4$ which was used here as a representative example for the presently claimed salts showed a significant effect on the structure of temperature denatured proteins. This is clearly an important finding. As denatured (unfolded or partially unfolded) proteins are more prone to associate to form aggregates than native proteins (Fink, A. L., 1998, Fold Des. 3(1):R9-R23), the results indicate that sodium sulphate can limit the tendency of rFSH molecules to denature and hence the risk for aggregation and thereby significantly increases the storage stability. Benzyl alcohol (BA) on the other hand induces significant structural decomposition at high temperatures. No ordered secondary structures were detected by SRCD. The observed effects of BA (more unfolded structures) may be part of the explanation for the increased aggregation found in other protein systems upon addition of benzyl alcohol (Maa, Y. and Hsu, C. C., 1996, Int. J. Pharm. 140:155-168; Zhang, Y. et al., 2004, J. Pharm. Sci. 93(12):3076-3089).

However, the addition of preservatives is crucial for the development of multidose formulations, and from the existence of rFSH products on the market it is known that more stable formulations need to be developed even with relatively high content of benzyl alcohol (Puregon® contains 10 mg/ml benzyl alcohol).

Benzyl alcohol was found to decrease the stability of rFSH and to favour loss of ordered secondary structures upon heating. However, an addition of preservatives is important. This study showed that the presently claimed salts increase the level of ordered structures in heated rFSH formulations. Thus, these salts are well suited as stabilizer(s) in a liquid rFSH formulation, for example to compensate for the effects of benzyl alcohol or other phenolic preservatives.

Example 2

Differential Scanning Calorimetry (DSC)

The FSH used representatively in this example is the same as in Example 1.

In general the native (bioactive) structure of proteins is very sensitive towards its surroundings e.g. the composition of the formulation, the container systems, pH and temperature. In the present example the rFSH denaturation temperature, $T_m$, has been investigated by liquid Differential Scanning Calorimetry (DSC). The rFSH denaturation temperature gives an indication of the stability of the protein in solution, where a higher $T_m$ indicates a more stable protein.

The tertiary and quaternary structure of proteins is stabilized mainly by non-covalent interactions. Since many of these intramolecular interactions are replaced by non-covalent interactions with water molecules during unfolding the thermodynamic balance between the different structural forms (i.e. native and denatured) is subtle. In general this means that the stability of native proteins is limited. Many proteins thermally unfold around 70° C. Protein folding or denaturation can be described by thermodynamic parameters which can be directly studied and quantified using DSC. Hence, DSC is an important tool to study the effects of excipients on protein stability, and thus to identify optimal formulations for protein therapeutics.

Liquid Differential Scanning Calorimetry (DSC)

Theory

When heating a protein sample (i.e. increasing the sample temperature) in a liquid DSC, only a slight increasing baseline is obtained, but when the heating continues (i.e. continued increase in temperature), heat is absorbed by the protein causing it to thermally unfold over a temperature range characteristic of the studied protein. This gives rise to an endothermic peak. During the protein unfolding, water molecules surrounding the protein reorganise since more hydrophobic chains are exposed. When the unfolding is complete, the heat absorption decreases and a new baseline is formed.

Integration of the heat capacity, $C_p$, of the sample gives the enthalpy change, $\Delta H$, associated with the unfolding process of equation (1). The enthalpy change observed originates from endothermic processes such as breaking of hydrogen bonds and exothermic processes such as formation of hydrogen bonds between the protein and the surrounding media. The midpoint of the thermal transition or transition midpoint, $T_m$ (often called the protein denaturation temperature), is the temperature when half of the protein molecules are folded and half of the protein molecules are unfolded.

$$\Delta H = \int_{T_1}^{T_2} C_p dT \qquad (1)$$

The raw data from the DSC measurements, that is, heat rate (in W) as a function of temperature could easily be recalculated to partial molar heat capacity (in J/mol K), knowing the molar mass and the concentration of the protein used.

Test Method

The protein denaturation temperature, $T_m$, was measured using a liquid DSC, Nano DSC from TA Instruments, equipped with 300 µl dual-capillary cells and using the following parameters: Scan rate: 0.5-2.0° C./min, if nothing else is stated, a scan rate of 1.0° C./min is used (2.0° C./min for ex. 4)

Start temperature: 20° C.
Final temperature: 100° C.
Equilibrium: 900 s (or 900 s (first scan) 600 s (second scan) for ex 4)
Constant pressure: 3 atm
All samples were degassed for 15 min before measurements. The sample cells were cleaned with 50% formic acid after each protein samples. Additionally the cells were rinsed with 1000 ml purified water after each sample run.

All samples were measured with the corresponding placebo in the reference cell. The results from a separate scan with the placebo solution filled in both reference and sample cell were subtracted from the data before evaluation, i.e. a blank subtraction.

MALDI-TOF MS

Samples of rFSH, before and after treatment with the enzyme sialidase, were analysed by Matrix Assisted Laser Desorption/Ionisation Time of Flight Mass Spectrometry (MALDI-ToF MS) to assess the extent of the desialylation reaction. Spectra were acquired on an Autoflex II MALDI ToF Mass Spectrometer (Bruker Daltonics). Sinapic acid was used as matrix. Analysis was performed in the positive linear ion mode, with delayed extraction. A scan range of 4000-20893 Da was used with external calibration.

The Object of this Example

The aim of this example was to investigate the thermal stability of rFSH by means of liquid Differential Scanning Calorimetry (DSC), and to study the stabilising effect of various salts on rFSH with and without addition of a preservative (phenol or benzyl alcohol).

This study together with previous Circular Dichroism (CD) spectroscopy studies (Example 1 above) and real time stability studies (Example 3 below) all aim to study the effect of salts and preservatives on the rFSH stability in solutions.

Products to be Studied rFSH Batch Information rFSH, drug substance batch no. 08800020 and batch no. 09PD80010 were manufactured by Bio-Technology General (BTG), Israel.

Determination of the biological activity of rFSH is performed according to Ph. Eur. The concentration was determined to be 13,223 IU/mg (resulting in 9,256 IU/ml) for batch 08800020 and 15,109 IU/mg (resulting in 10,576 IU/ml) for batch 09PD80010, respectively for the two rFSH batches used.

Materials

Excipients

A list of the excipients used in the rFSH solutions in this study is listed in Table 2.

TABLE 2

List of excipients

| Name | Supplier |
|---|---|
| Di-sodium hydrogen phosphate × 2H$_2$O, Ph. Eur. | Merck |
| Phosphoric acid 85%, Ph. Eur. | Merck |
| Sodium chloride, Ph. Eur. | Merck |
| Di-sodium sulphate × 10H$_2$O, Ph. Eur. | Merck |
| Magnesium chloride × 6H$_2$O, Ph. Eur. | Merck |
| Potassium chloride, p.a. | Merck |
| Sodium iodide, Ph. Eur. | Merck |
| Ammonium sulphate, Ph. Eur. | Merck |
| Potassium iodide, Ph. Eur. | Merck |
| Zinc chloride, Ph. Eur. | Riedel-de-Haën |
| Tri-sodium citrate × 2H$_2$O, Ph. Eur. | Merck |
| Ammonium acetate, Ultra >99.0% | Fluka |
| Sodium acetate, × 3H$_2$O, Ph. Eur. | Merck |
| Sodium perchlorate × H$_2$O, p.a. | Merck |
| Zinc iodide, p.a. | Merck |
| Zinc sulphate, Ph. Eur. | Merck |
| Di-potassium sulphate, Ph. Eur. | Merck |
| Di-sodium tartrate × 2H$_2$O, p.a. | Merck |
| Ammonium iodide, p.a. | Merck |
| Sucrose, Ph. Eur. | Merck |
| Di-potassium hydrogen phosphate × 3H$_2$O, p.a. | Merck |
| Magnesium sulphate × 7H$_2$O, Ph. Eur. | Fluka |
| Polysorbate 20 (Tween 20) Ph. Eur. | Merck |
| Phenol, Ph. Eur. | Merck |
| Benzyl alcohol, Ph. Eur. | Merck |
| L-methionine, Ph. Eur. | Sigma |
| Milli-Q water | Millipore |

Composition of Tested Solutions

The composition of the tested rFSH and placebo solutions are listed in Table 3, Table 4 and Table 5. The tested concentration of the preservatives is chosen based on the concentration required to fulfil the Ph. Eur. A criteria concerning preservation efficacy of a formulation aimed for parenteral use.

The salt concentrations tested are based on the concentration of sodium sulphate needed to obtain isotonicity in the tested solutions, that is, 0.1 M sodium sulphate. All other salts are tested at the same molar concentration as sodium sulphate. Additionally a higher and lower concentration of sodium chloride is tested, to evaluate the effect of the salt concentration on the rFSH denaturation temperature, $T_m$.

The sodium phosphate buffer concentration in the tested solutions is kept low to minimise the risk of stabilising/destabilising effects of the buffer salts as such.

TABLE 3

Composition of rFSH solutions

| rFSH | Buffer | Surfactant | Preservative | Antioxidant | Stabiliser |
|---|---|---|---|---|---|
| 2.4 mg/ml | 1 mM Phosphate buffer pH 5.5 or pH 6.5 or pH 7.5 | 0.005 mg/ml Polysorbate 20 | 5 mg/ml Phenol or 15 mg/ml Benzyl alcohol or none | 0.5 mg/ml L-methionine | 0.1M Na$_2$SO$_4$ or 0.24M NaCl or 0.1M NaCl or 0.07M NaCl or 0.1M Na-acetate or 0.1M Na$_3$-citrate or 0.1M Na$_2$-tartrate or 0.1M NaI or 0.1M NaClO$_4$ or 0.1M K$_2$SO$_4$ or 0.1M K$_2$HPO$_4$ or 0.1M KCl or 0.1M KI or |

TABLE 3-continued

Composition of rFSH solutions

| rFSH | Buffer | Surfactant | Preservative | Antioxidant | Stabiliser |
|------|--------|------------|--------------|-------------|------------|
|      |        |            |              |             | 100 mM $(NH_4)_2SO_4$ or 0.1M $NH_4$-acetate or 0.1M $NH_4I$ or 0.1M $MgSO_4$ or 0.1M $MgCl_2$ or 0.1M $ZnSO_4$ or 0.1M $ZnCl_2$ or 0.1M $ZnI_2$ or 0.1M sucrose or None |

TABLE 4

Composition of de-sialylated rFSH solutions

| De-sialylated rFSH | Buffer | Surfactant | Antioxidant | Stabiliser |
|---|---|---|---|---|
| 2.4 mg/ml | 1 mM Phosphate buffer pH 6.5 | 0.005 mg/ml Polysorbate 20 | 0.5 mg/ml L-methionine | 0.1M $Na_2SO_4$ or 0.1M $NaClO_4$ or None |

TABLE 5

Composition of placebo solutions

| Buffer | Surfactant | Preservative | Antioxidant | Stabiliser |
|---|---|---|---|---|
| 1 mM Phosphate buffer pH 5.5 or pH 6.5 or pH 7.5 | 0.005 mg/ml Polysorbate 20 | 5 mg/ml Phenol or 15 mg/ml Benzyl alcohol or none | 0.5 mg/ml L-methionine | 0.1M $Na_2SO_4$ or 0.24M NaCl or 0.1M NaCl or 0.07M NaCl or 0.1M Na-acetate or 0.1M $Na_3$-citrate or 0.1M $Na_2$-tartrate or 0.1M NaI or 0.1M $NaClO_4$ or 0.1M $K_2SO_4$ or 0.1M $K_2HPO_4$ or 0.1M KCl or 0.1M KI or 100 mM $(NH_4)_2SO_4$ or 0.1M $NH_4$-acetate or 0.1M $NH_4I$ or 0.1M $MgSO_4$ or 0.1M $MgCl_2$ or 0.1M $ZnSO_4$ or 0.1M $ZnCl_2$ or 0.1M $ZnI_2$ or 0.1M sucrose or None |

Manufacturing Procedure

All solutions (Table 3, Table 4 and Table 5) are manufactured at lab-scale at Ferring Pharmaceuticals A/S, Copenhagen, Denmark. The manufacturing procedure is summarized below:

rFSH Stock Solution Preparation

The rFSH stock solutions in phosphate buffer are prepared by adding a concentration step using rFSH batch 08800020 or batch 09PD80010 drug substance solution as starting material. The up concentration is performed using a Vivaspin 20 device with a 10 kDa molecular weight membrane cut off (MWCO) from Vivascience. The membrane is pre-washed by centrifuging 15 ml of the corresponding placebo solution, containing 0.5 mg/ml L-methionine, 0.005 mg/ml Polysorbate 20 in 1 mM phosphate buffer pH 5.5, 6.5 or 7.5 through the filter. The centrifugation is performed at 3000×g for 20 minutes using a swing-out rotor.

To perform the concentration step, a total of 80 ml of rFSH sample is used to fill four Vivaspin 20 devices (20 ml per device) and centrifuged at 3000×g for 15 min. Each retenate is transferred to a 20 ml volumetric flask. The filters are washed with small aliquots of the desired placebo solution. The washing solution is transferred to the volumetric flask, which is finally diluted to volume using the same placebo solution. This results in a 2.8 mg/ml rFSH stock solution containing 0.5 mg/ml L-methionine, 0.005 mg/ml Polysorbate 20 in a 1 mM phosphate buffer pH 5.5, 6.5 or 7.5, respectively.

Preparation of rFSH and Placebo Solutions

Stock solutions of all excipients, except the preservatives, are prepared in Milli-Q water.

For preparation of rFSH and placebo solutions, stock solutions of each excipient are mixed to obtain the desired concentrations given in Table 3, Table 4 and Table 5. The preservative is added directly to the solutions.

De-Sialylation of rFSH

The concentrated rFSH solution having an rFSH concentration of 2.8 mg/ml containing 0.5 mg/ml L methionine, 0.005 mg/ml Polysorbate 20 in a 1 mM phosphate buffer pH 6.5 is used to remove the sialic acid from the sugar moieties attached to rFSH.

The removal is done enzymatically, using an $\alpha(2\rightarrow3,6,8,9)$ Neuraminidase (a sialidase) from Sigma. The rFSH is treated with the Neuraminidase during overnight shaking at 37° C. The reagents are removed using Vivaspin devices as described above for concentration of rFSH. The rFSH solution containing the enzymes is transferred to a prewashed Vivaspin device. The device is centrifuged, the filtrate is discharged and the retenate is re-suspended in a placebo solution containing 0.5 mg/ml L methionine, 0.005 mg/ml Polysorbate 20 in a 1 mM phosphate buffer pH 6.5. The solution is centrifuged again. This procedure is repeated three times before the final retenate is transferred to a volumetric flask and diluted to volume with the placebo solution. This yields a 2.8 mg/ml desialylated rFSH stock solution containing 0.5 mg/ml L methionine, 0.005 mg/ml Polysorbate 20 in a 1 mM phosphate buffer pH 6.5.

Results and Discussion

Effect of DSC Scanning Speed on rFSH $T_m$

To investigate the effect of the DSC scanning speed on the rFSH denaturation temperature, $T_m$ measurements are performed with three different scanning speeds. As can be seen in Table 6, the rFSH $T_m$ varies with the DSC scan rate used during the measurements.

As long as denaturation temperatures obtained from measurements performed with identical scan rates are compared, the fact that $T_m$ varies with the scan rate does not affect the interpretation of the data, see for example Table 7.

TABLE 6

Denaturation temperature, $T_m$, in relation to scan rate for rFSH samples containing 2.4 mg/ml rFSH, 0.5 mg/ml L methionine, 0.005 mg/ml Polysorbate 20 in a 1 mM sodium phosphate buffer pH 6.5.

| Scan rate | $T_m$ | |
|---|---|---|
| 0.5° C./min | 71.9° C. | |
| 1.0° C./min | 72.9° C. | |
| 2.0° C./min* | 74.9° C. | Mean = |
| 2.0° C./min* | 74.3° C. | 74.6° C. |

*Duplicate sample preparation and analyses

Figure 4:
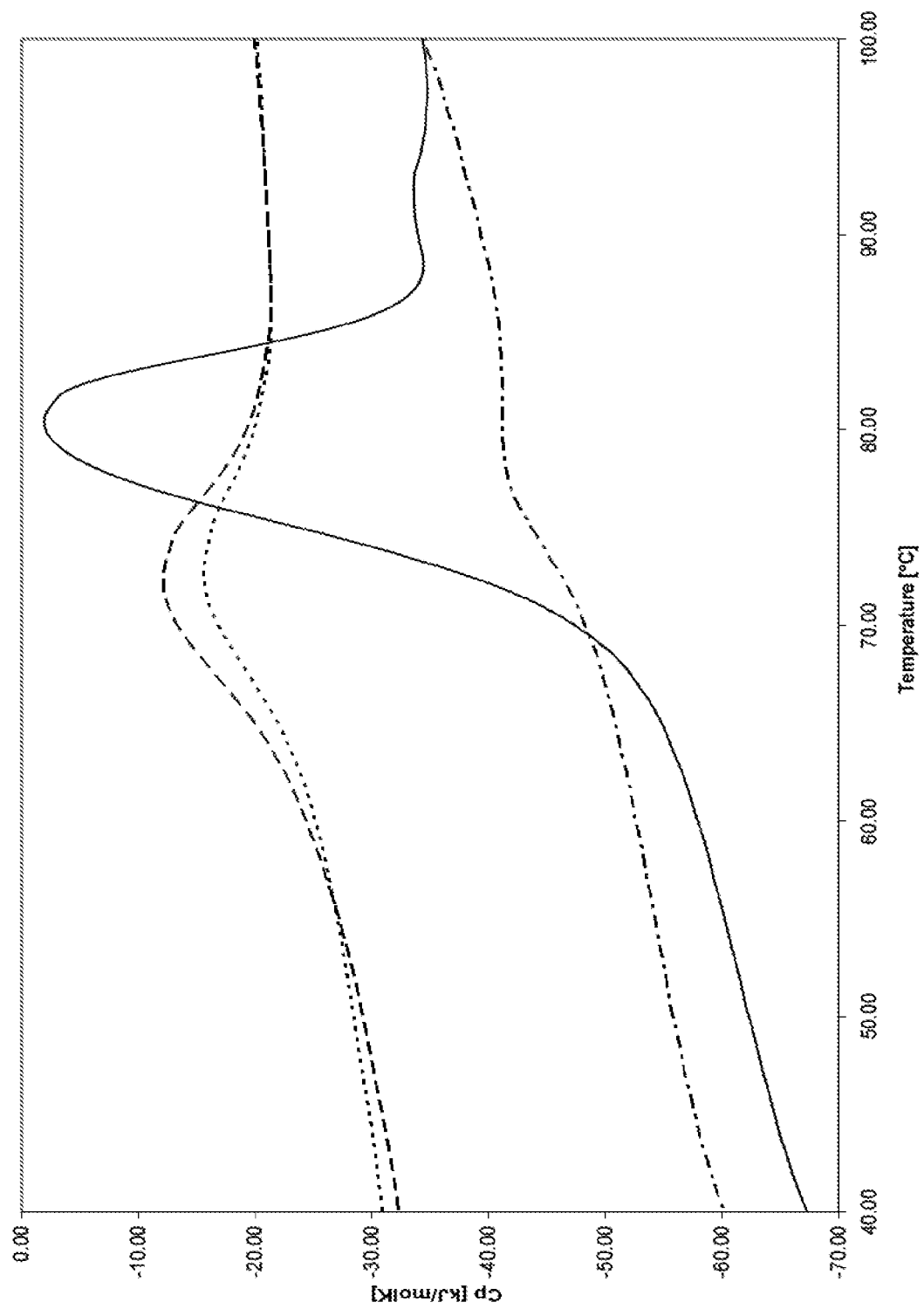

Repeating DSC scans up to 100° C. have shown that denaturation of rFSH is partly irreversible under the experimental conditions (see FIG. 4). This means that refolding is slower than the equilibration time between two DSC scans, or that unfolding is associated with an irreversible step as indicated in equation 2.

$$\text{Native} \leftrightarrow \text{Unfolded} \rightarrow \text{Irreversibly Dentaured} \quad (2)$$

Effect of Addition of a Preservative on rFSH $T_m$

As can be seen in Table 7, addition of a preservative to a rFSH solution, lowers the denaturation temperature, $T_m$, with 2-6° C., depending on the preservative used. This corresponds well to previously reported data both for other recombinant proteins and for urinary derived FSH.

The larger decrease in $T_m$ obtained for rFSH solutions with benzyl alcohol in comparison to rFSH solutions with phenol (see Table 7) could be explained from the higher concentration of benzyl alcohol (15 mg/ml) than phenol (5 mg/ml) used in the experiments.

TABLE 7

Denaturation temperature with and without addition of a preservative, $T_{m(preservative)}$ and $T_{m(no\ preservative)}$, for rFSH samples containing 2.4 mg/ml rFSH, 0.5 mg/ml L-methionine, 0.005 mg/ml Polysorbate 20, 1 mM sodium phosphate buffer pH 6.5 and the excipients listed in the table. $\Delta T_{m(preservative)} = T_{m(preservative)} - T_{m(no\ preservative)}$

| Preservative | Salt | $T_{m(no\ preservative)}$ | $T_{m(preservative)}$ |
|---|---|---|---|
| 5 mg/ml phenol | No salt | 72.9° C.* | 70.2° C.* |
| | | 74.9° C.** | 72.3° C.** |
| 15 mg/ml benzyl alcohol | No salt | 74.9° C.** | 70.1° C.** |
| 5 mg/ml phenol | 0.1M Na$_2$SO$_4$ | 78.0° C. | 75.1° C.* |
| 15 mg/ml benzyl alcohol | 0.1M Na$_2$SO$_4$ | 78.9 C.** | 73.3° C. |

*Calculated from DSC measurements performed with a scan rate of 1.0° C./min.
**Calculated from DSC measurements performed with a scan rate of 2.0°/min.

Effect of Addition of Various Salts on rFSH $T_m$

Ranking salts according to their general effects on protein solubility and stability is known as the Hofmeister series or lyotropic series, equation (3) below. The salting-out agents to the left-hand side, the so called kosmotropic ions are known to yield a stabilising effect on the proteins. Whereas the chaotropic or salting-in ions to the right-hand side, are known to destabilise proteins.

$$SO_4^{2-}>HPO_4^{2-}>F^->Cl^->Br^->NO_3^->I^-> ClO_4^->SCN^- \quad (3)$$

Effect of Addition of Various Salts to Solutions without Preservative on rFSH $T_m$ When measuring the effect of various sodium salts on rFSH $T_m$, quite surprisingly, the stabilising/destabilising effect expected according to the Hofmeister series as described above were not observed, when varying the cations see Table 8 and Table 9. Regardless of whether the most kosmotropic ion, sulphate, or the chaotropic ion, perchlorate, were used, the increase in denaturation temperature was approximately the same. In fact, the largest increase in rFSH $T_m$ was obtained for salts of perchlorate ions, where a destabilising effect on rFSH is expected. The increase in $T_m$ was in the same range both for a variety of inorganic anions like sulphate, chloride and perchlorate but also for organic anions like citrate, acetate and tartrate.

TABLE 8

Denaturation temperature, $T_m$, in relation to combination of the salt anion and cation for rFSH samples containing 2.4 mg/ml rFSH, 0.5 mg/ml L methionine, 0.005 mg/ml Polysorbate 20, 1 mM sodium phosphate buffer pH 6.5 and 0.1M salt.

| | Cation | | | | |
|---|---|---|---|---|---|
| Anion | K$^+$ | Na$^+$ | NH$_4^+$ | Mg$^{2+}$ | Zn$^{2+}$ |
| SO$_4^{2-}$ | 77.6° C. | 78.0° C. | 74.9° C. | 75.0° C. | 60.2° C. |
| HPO$_4^{2-}$ | 77.9° C. | | | | |
| Acetate | | 77.7° C. | 76.2° C. | | |
| Citrate | | 78.4° C. | | | |
| Tartrate | | 78.4° C. | | | |
| Cl$^-$ | 77.6° C. | 77.7° C. | | 74.4° C. | 59.9° C. |
| I$^-$ | 78.3° C. | 78.7° C. | 76.3° C. | | 57.5° C. |
| ClO$_4^-$ | | 80.3° C. | | | |

No added salt: $T_m$ = 72.9° C., other excipients according to the table header
0.1M Sucrose: $T_m$ = 73.3° C., other excipients according to the table header

TABLE 9

Change in denaturation temperature, $\Delta T_{m(salt)}$, in relation to combination of the salt anion and cation for rFSH samples containing 2.4 mg/ml rFSH, 0.5 mg/ml L-methionine, 0.005 mg/ml Polysorbate 20, 1 mM sodium phosphate buffer pH 6.5 upon addition of 0.1M salt. $\Delta T_{m(salt)} = T_{m(salt)} - T_{m(no\ salt)}$.

| | Cation | | | | |
|---|---|---|---|---|---|
| Anion | K$^+$ | Na$^+$ | NH$_4^+$ | Mg$^{2+}$ | Zn$^{2+}$ |
| SO$_4^{2-}$ | 4.7° C. | 5.1° C. | 2.1° C. | 2.1° C. | -12.7° C. |
| HPO$_4^{2-}$ | 5.0° C. | | | | |
| Acetate | | 4.8° C. | 3.3° C. | | |
| Citrate | | 5.5° C. | | | |
| Tartrate | | 5.5° C. | | | |
| Cl$^-$ | 4.7° C. | 4.8° C. | | 1.5° C. | -13.0° C. |
| I$^-$ | 5.5° C. | 5.8° C. | 3.4° C. | | -15.4° C. |
| ClO$_4^-$ | | 8.0° C. | | | |

0.1M Sucrose: 0.4° C., other excipients according to the table header

The observed trend, that the position of the anions in the Hofmeister series does not affect the increase of rFSH $T_m$ upon addition of different sodium salts, is also found for potassium (see Table 8 and Table 9). Having the same cation, the anion in general only influences the change in rFSH $T_m$ to a minor degree and never according to the Hofmeister series.

Quite surprisingly, the cations, on the other hand, do influence the rFSH Tm. More specifically, salts with monovalent cation display in general a higher rFSH $T_m$ than divalent ions (see Table 8). Especially, the monovalent alkali metal ions give rise to a high rFSH $T_m$. In other words, the observed stabilising effects (i.e. the increase in rFSH $T_m$) upon addition of salt is quite independent of the anions tested (see Tables 8 and 9), whereas the cations have a large influence on the degree of stabilisation. Salts of potassium and sodium display a particularly large stabilising effect.

All above tested solutions have a salt concentration of 0.1 M. To investigate the effect of the salt concentration on the rFSH $T_m$, DSC measurements of rFSH solutions containing three different sodium chloride concentrations were investigated. The stabilising effect upon addition of salt to an rFSH solution is observed in the whole range of salt concentration tested (see Table 10).

TABLE 10

Change in denaturation temperature, $\Delta T_{m(salt)}$, for rFSH samples containing 2.4 mg/ml rFSH, 0.5 mg/ml L-methionine, 0.005 mg/ml Polysorbate 20, 1 mM sodium phosphate buffer pH 6.5 upon addition of different sodium chloride concentrations.
$\Delta T_{m(salt)} = T_{m(salt)} - T_{m(no\ salt)}$

| NaCl concentration | $\Delta T_{m(salt)}$ |
|---|---|
| 0.07M | 4.2° C.** |
| 0.1M | 4.8° C.* |
| 0.24M | 5.4° C.** |

*Calculated from DSC measurements performed with a scan rate of 1.0° C./min.
**Calculated from DSC measurements performed with a scan rate of 2.0° C./min.

Existing patents on FSH formulations use e.g. sucrose as stabilisers for FSH. Addition of 0.1 M sucrose to a rFSH solution yields a minute change in rFSH $T_m$ (see Table 8 and Table 9), indicating that the stabilising effect of rFSH upon addition of potassium or sodium salts are markedly higher than the effect obtained upon addition of sucrose.

Effect of Addition of Various Salts to Solutions with Added Preservative on rFSH $T_m$ It is well known that addition of preservatives to protein solutions decrease the protein stability in solution. However, for an aqueous multidose formulation aimed for parenteral use, a preservative is a requirement. Therefore it is of vast importance to compensate for the decrease in protein stability upon addition of preservative by addition of stabilisers, like salts, to the rFSH solutions.

TABLE 11

Denaturation temperature, $T_m$, and changes in denaturation temperature, $\Delta T_{m(preservative)}$ and $\Delta T_{m(salt)}$ for rFSH samples containing 2.4 mg/ml rFSH, 5 mg/ml phenol, 0.5 mg/ml L methionine, 0.005 mg/ml Polysorbate 20, 1 mM sodium phosphate buffer pH 6.5 and 0.1M salt as given in the table.
Here $\Delta T_{m(preservative)} = T_{m(preservative)} - T_{m(no\ preservative)}$ and $\Delta T_{m(salt)}^* = T_{m(salt)} - T_{m(no\ salt)}$.

| | $T_m$ | $\Delta T_{m(preservative)}$ | $\Delta T_{m(salt)}^*$ |
|---|---|---|---|
| No salt | 70.2° C. | −2.7° C. | — |
| Na$_2$SO$_4$ | 75.1° C. | −2.9° C. | 4.9° C. |
| NaCl | 74.7° C. | −2.9° C. | 4.6° C. |
| NaClO$_4$ | 78.6° C. | −2.3° C. | 8.4° C. |

*For rFSH solutions containing 5 mg/ml phenol

As can be seen in Table 11, adding a preservative to an rFSH solution results in a lowering of the rFSH denaturation temperature with 2-3° C. Addition of salt to preserved rFSH solutions increases the rFSH denaturation temperature with around 5° C. In other words, the destabilising effect observed upon addition of a preservative to an rFSH solution is well compensated for by addition of a salt as defined by the invention. Actually, the addition of salt to rFSH solutions containing phenol does not only neutralise the effect of the preservative on the rFSH $T_m$, it actually increases the $T_m$ compared to rFSH in aqueous solution without addition of preservative or salt (see Table 11).

Effect of Altering the pH on rFSH $T_m$

To study the effect of pH on the rFSH $T_m$ with and without addition of stabilising salts, the rFSH denaturation temperature was determined at a pH of 5.5, 6.5 and 7.5 with and without addition of three different sodium salts (see Table 12).

TABLE 12

Denaturation temperature, $T_m$, at different pHs for rFSH samples containing 2.4 mg/ml rFSH, 0.5 mg/ml L methionine, 0.005 mg/ml Polysorbate 20, 1 mM sodium phosphate buffer and 0.1M salt. Here $\Delta T_{m(salt)} = T_{m(salt)} - T_{m(no\ salt)}$

| | $T_m$ | | | $\Delta T_{m(salt)}$ | | |
|---|---|---|---|---|---|---|
| | pH 5.5 | pH 6.5 | pH 7.5 | pH 5.5 | pH 6.5 | pH 7.5 |
| No salt | 70.5° C. | 72.9° C. | 74.9° C. | — | — | — |
| Na$_2$SO$_4$ | 76.2° C. | 78.0° C. | 78.7° C. | 5.7° C. | 5.1° C. | 3.8° C. |
| NaCl | 75.0° C. | 77.7° C. | 78.6° C. | 4.5° C. | 4.8° C. | 3.7° C. |
| NaClO$_4$ | 78.6° C. | 80.9° C. | 81.7° C. | 8.1° C. | 8.0° C. | 6.7° C. |

As can be seen in Table 12, the general trends in rFSH $T_m$ upon addition of different sodium salts is the same over the whole pH range from 5.5 to 7.5, that is, the deviation from the stabilising/destabilising effect of salts according to the Hofmeister series is observed at all tested pH.

In the investigated pH range, the observed rFSH denaturation temperatures are increasing with increasing pH in solutions, both with and without addition of salt (see Table 12). The actual increase in rFSH denaturation temperature upon addition of salts, $\Delta T_{m\ (salt)}$, is slightly lower at the higher pH (see Table 12).

Effect of rFSH Sialylation on rFSH $T_m$

As has been shown above, the influence of the addition of salts to a rFSH solution does not at all follow the, above-described, Hofmeister series, where salts of perchlorate ions are expected to destabilise proteins (yield a lower protein $T_m$) and sulphate ions are expected to stabilise proteins (yield a higher protein $T_m$).

Since rFSH is a glycosylated protein, having numerous sialic acid residues attached to the sugar moieties, and hence a fairly high negative net charge, the effect of the sialic acid on the unexpected stabilising behaviour of the salts was investigated.

To study the effect of the sialic acid on rFSH $T_m$ upon addition of different salts, the sialic acid was removed enzymatically. The de-sialylated rFSH was then analysed by means of DSC, with and without addition of salt.

To verify that the sialic acid residues were removed successfully, the rFSH sample before and after the enzymatic removal of sialic acid were analysed by means of MALDI-ToF MS. Under MALDI-ToF MS acid sample conditions the alpha- and the beta-subunits are dissociated and therefore measured separately. The average molecular weight of the alpha-subunit before treatment with sialidase is 15000 Da. After treatment with sialidase the average molecular weight is 14000 Da. The average molecular weight of the beta-subunit before treatment with sialidase is 18000 Da, and 17000 Da after treatment with sialidase. The shift in mass for both subunits is a result of removal of sialic acids which results in mass reduction. Practically all sialic acid residues were removed from rFSH during the desialylation.

The increase of rFSH $T_m$ upon addition of sodium sulphate or sodium perchlorate follows the same trend for unmodified rFSH and de-sialylated rFSH, that is, the stabilising effect (increase in rFSH $T_m$) observed do not follow the above-described Hofmeister series. In general the observed $T_m$ is 2-6° C. lower for de-sialylated rFSH than for unmodified rFSH (see Table 13). The stabilising effect observed upon addition of salt is also lower for de-sialylated rFSH than for unmodified rFSH (see Table 13).

The lower $T_m$ obtained for de-sialylated rFSH than for unmodified rFSH is expected, since the presence of sialic acid on the sugar moieties on rFSH is believed to increase the rFSH stability.

The fact that both unmodified rFSH and de-sialylated rFSH follow the same trend (deviating from the stabilising/destabilising effect according to the Hofmeister series) upon addition of various salts, proves that it is not the presence of sialic acids on rFSH per se that gives rise to this effect.

TABLE 13

Denaturation temperature, $T_m$, for rFSH and de-sialylated rFSH samples containing 2.4 mg/ml rFSH or 2.4 mg/ml de-sialylated rFSH, 0.5 mg/ml L methionine, 0.005 mg/ml Polysorbate 20, 1 mM sodium phosphate buffer pH 6.5 and 0.1M salt. Here, $\Delta T_{m(salt)} = T_{m(salt)} - T_{m(no\ salt)}$.

|  | $T_m$ | | $\Delta T_{m(salt)}$ | |
| --- | --- | --- | --- | --- |
|  | rFSH | De-sialylated rFSH | rFSH | De-sialylated rFSH |
| No salt | 72.9° C. | 70.7° C. | — | — |
| Na$_2$SO$_4$ | 78.0° C. | 72.1° C. | 5.1° C. | 1.5° C. |
| NaClO$_4$ | 89.9° C. | 75.0° C. | 8.0° C. | 4.4° C. |

CONCLUSIONS

The destabilising effect (lowering of rFSH $T_m$) observed for rFSH upon addition of preservative corresponds well to state of the art knowledge within the area.

The observed deviation from the Hofmeister series in the rFSH denaturation temperature upon addition of salts with different anions, is however unexpected. According to the Hofmeister series, (which ranks salts according to their general effects on protein solubility and stability), kosmotropic anions like sulphate normally stabilise proteins (yield a higher $T_m$) whereas chaotropic anions like perchlorate destabilise proteins (yield a lower $T_m$). In this study all tested anions having the same cation, display a similar increase in the rFSH denaturation temperature. Quite opposite to the prediction from the Hofmeister series, salts of perchlorate ions display the largest increase in rFSH denaturation temperature.

In other words, the observed stabilising effect (i.e. the increase in rFSH $T_m$) upon the addition of salt is quite independent of the anions tested. Salts of sodium and potassium display particularly large stabilising effect. Especially the addition of sodium perchlorate to an rFSH solution gives rise to a large increase in rFSH denaturation temperature. However, perchlorates are generally highly reactive and are oxidising agents and perchlorates are therefore not approved as inactive ingredients in pharmaceutical formulations.

The unexpected stabilising effect obtained for rFSH upon addition of salts cannot be explained by the presence of sialic acid on the sugar moieties of rFSH. rFSH denaturation temperature determinations on de-sialylated rFSH display the same trends in the stabilising effect on rFSH upon addition of salts as unmodified rFSH.

Example 3

Real Time Stability on rFSH Solutions

Aim of the Study

The objective of this study was to establish if the real time stability of rFSH in various formulations follows the same trend as seen in the measurements of rFSH denaturation temperature by means of liquid DSC as described in Example 2 and also the changes in rFSH secondary structure upon heating as measured with CD spectroscopy, as described in Example 1. The structural stability of rFSH during storage, measured as how prone rFSH is to dissociate into its monomers is determined in this study.

The stability of rFSH 600 IU/ml formulations after storage at two different storage temperatures was studied at long term 5±3° C./ambient RH and accelerated 30±2° C./65±5% RH conditions for 6-12 months. All vials were stored in inverted position.

Placebo controls containing the corresponding formulations but with no added rFSH were stored under the same conditions as described for active rFSH.

Product to be Studied

Batch Information rFSH, drug substance batch no 08800060 and batch no 09800020 was manufactured by Bio-Technology General (BTG), Israel Determination of the biological activity of the above rFSH batches were performed according to Ph. Eur.

Materials

Excipients

A list of the excipients used in this study is described in Table 14.

TABLE 14

List of excipients

| Name | Supplier |
| --- | --- |
| Di-sodium hydrogen phosphate dihydrate, Ph. Eur. | Merck |
| Phosphoric acid 85%, Ph. Eur. | Merck |
| Sucrose, Ph. Eur. | Merck |
| Polysorbate (polysorbate) 20 Ph. Eur. | Merck |
| Phenol, Ph. Eur. | Merck |
| L-methionine, Ph. Eur. | Sigma |
| Sodium chloride, Ph. Eur. | Merck |
| Di-sodium sulphate x 10H$_2$O, Ph. Eur. | Merck |
| Milli-Q water | Millipore |

Container and Closure System

The primary packing materials used are listed in Table 15.

TABLE 15

Container/closure system

| Item | Description | Supplier |
| --- | --- | --- |
| Container | Type 1 Ph. Eur. Colourless borosilicate glass vials, 2R | ISO-GmbH |
| Rubber | 13 mm chlorobutyl stopper 4432/50 B2-40 coated, FluoroTec | West Pharmaceutical Services |

TABLE 15-continued

Container/closure system

| Item | Description | Supplier |
|---|---|---|
| Cap | Aluminium cap and plastic cap (flip off) | West Pharmaceutical Services |

The composition of the rFSH stock solutions and the different formulations (rFSH and placebo) are listed in Table 16, Table 17 and Table 18. Except for the formulation not containing any stabiliser/tonicity agent, the concentration of the stabiliser/tonicity agent is adjusted to give isotonic solutions.

TABLE 16

Composition of rFSH stock solutions

| Batch | rFSH concentration | Vehicle |
|---|---|---|
| 08800060 | 16235 IU/mg 0.7 mg/ml | 0.5 mg/ml L-methionine, 0.005 mg/ml Polysorbate 20 in 1 mM Disodium hydrogen phosphate pH 6.7-6.8 |
| 09800020 | 13223 IU/mg 0.7 mg/ml | 0.5 mg/ml L-methionine, 0.005 mg/ml Polysorbate 20 in 1 mM Disodium hydrogen phosphate pH 6.7-6.8 |

TABLE 17

Composition of the rFSH formulations

| rFSH | Buffer | Surfactant | Preservative | Antioxidant | Stabiliser/tonicity agent |
|---|---|---|---|---|---|
| 600 IU/ml | 20 mM Phosphate pH 6.5* | 0.005 mg/ml Polysorbate 20 | — | 0.5 mg/ml L-methionine | 15 mg/ml Na$_2$SO$_4$ |
| 600 IU/ml | 1 mM Phosphate pH 6.5* | 0.005 mg/ml Polysorbate 20 | 5 mg/ml Phenol | 1 mg/ml L-methionine | 14 mg/ml Na$_2$SO$_4$ |
| 600 IU/ml | 1 mM Phosphate pH 6.5* | 0.005 mg/ml Polysorbate 20 | 5 mg/ml Phenol | 1 mg/ml L-methionine | 7 mg/ml NaCl |
| 600 IU/ml | 1 mM Phosphate pH 6.5* | 0.005 mg/ml Polysorbate 20 | 5 mg/ml Phenol | 1 mg/ml L-methionine | 75 mg/ml Sucrose |
| 600 IU/ml | 1 mM Phosphate pH 6.5* | 0.005 mg/ml Polysorbate 20 | 5 mg/ml Phenol | 1 mg/ml L-methionine | — |

*The pH refers to the pH of the final solution

TABLE 18

Composition of the placebo formulations

| Buffer | Surfactant | Preservative | Antioxidant | Stabiliser/tonicity agent |
|---|---|---|---|---|
| 20 mM Phosphate pH 6.5* | 0.005 mg/ml Polysorbate 20 | — | 0.5 mg/ml L-methionine | 15 mg/ml Na$_2$SO$_4$ |
| 1 mM Phosphate pH 6.5* | 0.005 mg/ml Polysorbate 20 | 5 mg/ml Phenol | 1 mg/ml L-methionine | 14 mg/ml Na$_2$SO$_4$ |
| 1 mM Phosphate pH 6.5* | 0.005 mg/ml Polysorbate 20 | 5 mg/ml Phenol | 1 mg/ml L-methionine | 7 mg/ml NaCl |
| 1 mM Phosphate pH 6.5* | 0.005 mg/ml Polysorbate 20 | 5 mg/ml Phenol | 1 mg/ml L-methionine | 75 mg/ml Sucrose |
| 1 mM Phosphate pH 6.5* | 0.005 mg/ml Polysorbate 20 | 5 mg/ml Phenol | 1 mg/ml L-methionine | — |

*The pH refers to the pH of the final solution

Manufacturing Procedure

All solutions (Table 17 and Table 18) are manufactured at lab-scale at Ferring Pharmaceuticals A/S, Copenhagen, Denmark. The manufacturing procedure is summarized below.

Preparation of rFSH and Placebo Formulations

Stock solutions of all excipients are prepared in Milli-Q water.

For preparation of placebo formulations, stock solutions of each excipient are mixed to obtain the concentrations given in Table 18. Before dilution to volume, the pH of each formulation is adjusted, when necessary.

For preparation of rFSH formulations, a dilution solution is prepared from the stock solution of each excipient. The pH of the dilution solutions is adjusted. Dilution solutions are mixed with the rFSH stock solution (see Table 16) to yield the final concentrations listed in Table 17.

Sterile Filtration and Aseptic Filling

The final formulations are sterile filtered using 0.22 μm PVDF filters (Millipore). Placebo formulations are sterile filtered into autoclaved glass bottles using Stericup filters. The rFSH formulations are sterile filtered into autoclaved glass beakers using Sterivex-GV filters and sterile 20 ml Luer Lock syringes (Braun). Sterile filtration, filling and sealing of vials is performed in a LAF bench using autoclaved vials and rubber stoppers. Before and after filling, vials are purged with nitrogen gas, passing through a 0.20 μm Millex-FG PFTE filter (Millipore) for at least 6 seconds. The vials are filled with 1.5 ml sample per vial. All vials are aseptically filled and immediately closed with rubber stoppers and alumino flip-off caps.

Storage Conditions

Samples containing rFSH 600 IU/ml and placebo are stored for 6-18 months at 5±3° C./ambient RH. In addition, samples are stored for 6-18 months at accelerated conditions, 30±2° C./65±5% RH. At each storage temperature, the vials are stored in inverted positions. All vials are protected from light.

Stability Programs

The stability programs for rFSH 600 IU/ml and placebo are depicted in Table 19 below.

TABLE 19

Stability programme for rFSH liquid formulation 600 IU/ml and placebo, stored in inverted position

| | Storage time (months) | | | | | |
|---|---|---|---|---|---|---|
| Storage condition | 0 | 1 | 3 | 6 | 12* | 18* |
| 5 ± 3° C./ambient RH | X | — | — | X | X | X |
| 30 ± 2° C./65 ± 5% RH | X | X | X | X | X | X |

— No testing scheduled according to the stability programme
*Only tested for some formulations Analytical Methods The analytical method used in this study is described below. At each testing occasion, 2 vials of rFSH and 1 vial of corresponding placebo will be analyzed for each formulation.

Low Molecular Weight (LMW) Forms

The LMW forms of rFSH are determined by LC-UV utilising isocratic elution on a size exclusion (SEC) column. The analysis is performed using a silica based column with TRIS buffer as mobile phase and UV detection. The LMW forms of rFSH are peaks eluting with molecular weight lower (after) than that of the rFSH main peak. The LMW forms are determined as peak area percentage of the total peak area.

For samples containing preservative, the preservative is removed from the sample solution before entering the size exclusion column.

Results and Discussion

Dissociation of rFSH During Storage

Since rFSH loses its bioactivity upon dissociation of the non-covalently coupled monomers, a straightforward way to follow loss of rFSH activity due to monomer dissociation is to measure the amount of rFSH LMW form in solution. This information can be retrieved from SEC chromatography, where the LMW forms peak eluting after the rFSH main peak is known to originate from dissociated rFSH.

TABLE 20

The rFSH relative amount of LMW forms (%) as determined by SEC after storage at 30 ± 2° C./65 ± 5% RH. The full description of all formulations is listed in Table 17.

| Stabiliser | Preservative | Storage time (months) | | | | | |
|---|---|---|---|---|---|---|---|
| | | 0 | 1 | 3 | 6 | 12 | 18 |
| 15 mg/ml Na$_2$SO$_4$ | — | 1.5 | 2.5 | 1.7 | 2.4 | 3.0 | 2.7 |
| 14 mg/ml Na$_2$SO$_4$ | 5 mg/ml Phenol | 1.7 | 3.5 | 3.1 | 3.9 | 6.5 | 6.0 |
| 7 mg/ml NaCl | 5 mg/ml Phenol | 1.8 | 1.7 | 3.1 | 3.1 | 4.4 | N.P. |
| 75 mg/ml Sucrose | 5 mg/ml Phenol | 1.9 | 6.2 | 7.3 | 10.1 | N.P. | N.P. |
| — | 5 mg/ml Phenol | 2.0 | 7.7 | 16.9 | 23.4 | 32.2 | N.P. |

N.P. Not performed.

TABLE 21

The rFSH relative amount of LMW forms (%) as determined by SEC after storage at 5 ± 3° C./ambient RH. The full description of all formulations is listed in Table 17.

| Stabiliser | Preservative | Storage time (months) | | | |
|---|---|---|---|---|---|
| | | 0 | 6 | 12 | 18 |
| 15 mg/ml Na$_2$SO$_4$ | — | 1.5 | 1.5 | 1.0 | 0.8 |
| 14 mg/ml Na$_2$SO$_4$ | 5 mg/ml Phenol | 1.7 | 2.0 | 1.6 | 1.3 |
| 7 mg/ml NaCl | 5 mg/ml Phenol | 1.8 | 1.1 | 1.3 | N.P. |
| 75 mg/ml Sucrose | 5 mg/ml Phenol | 1.9 | 1.9 | N.P. | N.P. |
| — | 5 mg/ml Phenol | 2.0 | 1.1 | 1.7 | N.P. |

N.P. Not performed.

As can be seen in Table 20, freshly prepared rFSH solution containing different stabiliser, with and without added preservative reveal similar relative amount of dissociated rFSH (LMW forms). Since the quantification limit of the SEC method is 3% no unambiguous differentiation between formulations can be performed below this limit, meaning that the observed differences in LMW forms at the initial time point are within the limits of the method variation.

Already after one month's storage at 30±2° C./65±5% RH, the relative amount of dissociated rFSH has increased for samples containing phenol together with sucrose or no stabiliser, whereas samples containing sodium sulphate or sodium chloride did not display any significant increase in dissociated rFSH (see Table 20).

After six months storage at 30±2° C./65±5% RH, the rFSH sample containing phenol without added stabiliser contains more than 20% dissociated rFSH (LMW forms). The rFSH samples containing phenol having sucrose as stabiliser also display a marked increase of dissociated rFSH (more than 10% dissociated rFSH), whereas samples containing phenol stabilised with either sodium chloride or sodium sulphate only display a minute increase in dissociated rFSH (see Table 20). Samples not containing any preservative are most stable towards dissociation during storage; however, for an aqueous multidose formulation aimed at parenteral use, the addition of a preservative is required, therefore this formulation is solely added as a comparison.

After six months storage at 5±3° C./ambient RH, none of the tested rFSH formulations reveal an increase in the relative amount of dissociated rFSH (see Table 21). Though, at least 24 month storage at 5° C. and concomitant one month, preferably 3-4 months storage at room temperature, is required for a commercial product of rFSH to be successful.

rFSH Denaturation Temperature, Changes in Secondary Structure and Degree of Dissociation Since the aim of this example was to determine the correlation between real time stability study data, rFSH denaturation temperature determinations by means of DSC and rFSH secondary structure data determined by CD spectroscopy, part of the DSC data (see Example 2) and part of the CD data (see Example 1) are presented below. All details on presented DSC results are given in Example 2 and details on the CD data are given in Example 1.

TABLE 22

The rFSH relative amount (%) of LMW forms as determined by SEC after 6 months storage at 30 ± 2° C./65 ± 5% RH and the rFSH denaturation temperature, $T_m$, as determined by DSC. In the DSC study the concentration of the stabilisers is kept at 0.1M for all tested solutions as compared to the amount used in the real time stability study given in the table.

| Stabiliser | Preservative | SEC, LMW 6 months at 30 ± 2° C./ 65 ± 5% RH | DSC $T_m$ |
|---|---|---|---|
| 15 mg/ml Na$_2$SO$_4$ | — | 2.3 | 78.0° C. |
| 14 mg/ml Na$_2$SO$_4$ | 5 mg/ml Phenol | 3.9 | 75.1° C. |
| 7 mg/ml NaCl | 5 mg/ml Phenol | 3.1 | 74.7° C. |
| 75 mg/ml Sucrose | 5 mg/ml Phenol | 10.1 | — |
| — | 5 mg/ml Phenol | 23.4 | 70.2° C. |

As can be seen in Table 22, the rFSH denaturation temperature obtained by DSC correlates well with the real time stability data after six months storage at 30±2° C./65±5% RH, a similar correlation between DSC and real time stability as analysed by SEC has been presented previously for recombinant antibodies and recombinant glycoproteins (see e.g. Burton et al (2007), Pharm. Dev. Technol. 12:265-273 and Remmele et al (1998), Pharm. Res. 15:200-208). The rFSH solution without added preservative stabilised with sodium sulphate displays only a low degree of dissociated rFSH after storage for six months, it also displays a significant higher denaturation temperature than solutions containing a preservative. It can further be seen that for solutions containing a preservative (phenol) addition of a salt, either sodium chloride or sodium sulphate, yields a significant lower degree of dissociated rFSH after six months storage, than solutions containing sucrose or no stabiliser. The denaturation temperature for rFSH without added stabiliser is also significantly lower than rFSH $T_m$ for solutions containing salt. The rFSH denaturation temperature for solutions containing sucrose with addition of phenol has not been determined, however, as can be seen in Table 23, measurements of rFSH $T_m$ for solutions without added preservative, displays the same trend as real time stability data after six months storage at 30±2° C./65±5% RH (see Table 22). In conclusion, NaCl and $Na_2SO_4$ are significant better stabilizers than sucrose towards structural degradation. This is shown both by $T_m$ measurements (see Table 23) and real time stability data (see Table 22).

TABLE 23

The rFSH denaturation temperature, $T_m$, for solutions with no added preservatives determined by DSC; for more details see Example 2.

| Stabiliser | DSC, $T_m$ |
|---|---|
| 0.1M $Na_2SO_4$ | 78.0° C. |
| 0.1M NaCl | 77.7° C. |
| 0.1M Sucrose | 73.3° C. |

TABLE 24

Change in denaturation temperature, $\Delta T_m$ for rFSH samples containing 2.4 mg/ml rFSH, 0.5 mg/ml L-methionine, 0.005 mg/ml Polysorbate 20, 1 mM sodium phosphate buffer pH 6.5 when adding preservative or salt as listed in the table. Scan rate 2° C./min. $\Delta T_m = T_{m(preservative/salt)} - T_{m(no\ addition)}$

| Preservative | Salt | $\Delta T_m$ |
|---|---|---|
| 15 mg/ml benzyl alcohol | No Salt | −4.7° C. |
| 15 mg/ml benzyl alcohol | 0.1M $Na_2SO_4$ | −1.6° C. |
| No preservative | 0.1M $Na_2SO_4$ | +4.1° C. |
| No preservative | No salt | 0° C. |

No real time stability data for solutions containing benzyl alcohol as preservative have been determined, however, when comparing the rFSH denaturation temperature as determined by DSC and the changes in rFSH secondary structure upon heating as determined with CD spectroscopy, the same trend is observed (see Table 24). The secondary structure of rFSH for different protein samples has been determined; the secondary structure determined at 24° C. can be regarded as the native structure, and here no differences in rFSH secondary structure can be observed for rFSH solutions upon addition of either benzyl alcohol (at 0.17 mg/ml) or sodium sulphate. Though, when heating the solutions to 76.5° C., the observed loss in rFSH secondary structure varies with the added excipients. Addition of preservative (benzyl alcohol) gives rise to a larger loss of rFSH secondary structure than for rFSH solutions not containing any preservative, while addition of salt (sodium sulphate) yields a smaller loss of rFSH secondary structure than for rFSH solutions without added salt. A loss of ordered rFSH secondary structure can be interpreted as a partial or full denaturation of the protein.

Example 4

Differential Scanning Calorimetry (DSC) Data for hCG

Human Chorionic Gonadotropin (hCG) is a heterodimer protein consisting of two glycosylated monomers: a 92 amino acid α-subunit which is common for hCG, Follicle Stimulating Hormone (FSH), Luteinizing Hormone (LH) and Thyroid Stimulation Hormone (TSH), and a 145 amino acid β-subunit which is specific for hCG. The glycoprotein hormones, comprising FSH and hCG, all loose their bioactivity upon dissociation of the non-covalently coupled monomers. Results from stability analyses have indicated that instability of recombinant FSH (rFSH) is primarily based on dimer dissociation (decomposition of quaternary structure, and concomitant decrease in immunobinding response).

The objective of this example is to establish if the previously observed dependence of various sugars and salts on rFSH denaturation temperature, as determined with DSC, and as described in examples 1-3 above, is also observed for the very similar protein hCG. Additionally, the DSC denaturation temperature for hCG determined in this study is compared with previously published real time stability data (Samaritani, F. 1995, hCG liquid formulations. EP 0 814, 841).

The denaturation temperature of hCG was studied in the presence and absence of 0.1 M of various sodium salts or sucrose in a 1 mM phosphate buffer containing 0.5 mg/ml L-methionine and 0.005 mg/ml polysorbate 20. Four different sugar and salts are investigated; sucrose, sodium sulphate, sodium chloride and sodium perchlorate.

Urinary Derived Human Chorionic Gonadotropin (hCG)

hCG, drug substance, batch no. 2823287510 (7059 IU/mg) as purified from human urine from Massone S. A., Argentina was used. The material was stored refrigerated at 2-8° C.

Determination of the biological activity of the above hCG batch was performed according to Ph. Eur.

The rFSH and further materials were used as described in Examples 2-3.

TABLE 25

List of excipients

| Name | Supplier |
|---|---|
| Di-sodium hydrogen phosphate dihydrate, Ph. Eur. | Merck |
| Phosphoric acid 85%, Ph. Eur. | Merck |
| L-methionine, Ph. Eur. | Sigma |
| Polysorbate (Tween) 20 Ph. Eur. | Merck |
| Sucrose, Ph. Eur. | Merck |
| Sodium sulphate × $10H_2O$, Ph. Eur. | Merck |
| Sodium chloride, Ph. Eur. | Merck |
| Sodium perchlorate × $10H_2O$, p.a. | Merck |
| Milli-Q water | Millipore |

The composition of the different hCG formulations are listed in Table 26.

TABLE 26

Composition of hCG formulations

| hCG | Buffer | Surfactant | Antioxidant | Sugar/salt |
|---|---|---|---|---|
| 5 mg/ml* | 1 mM Phosphate pH 6.5 | 0.005 mg/ml Polysorbate 20 | 0.5 mg/ml L-methionine | 0.1M Na$_2$SO$_4$ |
| 5 mg/ml* | 1 mM Phosphate pH 6.5 | 0.005 mg/ml Polysorbate 20 | 0.5 mg/ml L-methionine | 0.1M NaCl |
| 5 mg/ml* | 1 mM Phosphate pH 6.5 | 0.005 mg/ml Polysorbate 20 | 0.5 mg/ml L-methionine | 0.1M NaClO$_4$ |
| 5 mg/ml* | 1 mM Phosphate pH 6.5 | 0.005 mg/ml Polysorbate 20 | 0.5 mg/ml L-methionine | 0.1M Sucrose |
| 5 mg/ml* | 1 mM Phosphate pH 6.5 | 0.005 mg/ml Polysorbate 20 | 0.5 mg/ml L-methionine | — |

*Corresponds to 35300 IU/ml for this batch.

Manufacturing Procedure

All solutions (Table 26) are manufactured at lab-scale at Ferring Pharmaceuticals A/S, Copenhagen, Denmark.

Preparation of hCG Formulations

Stock solutions of all excipients are prepared in Milli-Q water. Placebo solutions with the various excipients are prepared from the stock solution. The hCG drug substance is dissolved in the placebo solutions to obtain the concentrations given in Table 26. Since stability data for these formulations were not available, the DSC analyses are always performed on freshly prepared samples; within one hour from sample preparation.

As can be seen in FIG. 4 and Table 27, the denaturation temperature, Tm, for hCG is lower than the Tm for rFSH. Additionally, the enthalpy of the denaturation process (i.e. the size of the denaturation peak) is markedly smaller for hCG than for rFSH. Unlike for rFSH where the denaturation process is almost completely irreversible after heating rFSH samples to 100° C., the denaturation process after heating hCG to 100° C. is, to a larger extent, reversible (2).

Native ⇌ Unfolded → Irreversibly Dentatured     (2)

An explanation for the fact that the hCG denaturation process is, to a large extent, reversible in the timeframe of the DSC measurements, while this is not true for rFSH, could be if the two subunits in hCG are less prone to dissociate than in rFSH. If the subunits do not dissociate while heating the hCG samples the native structure could easier be re-formed again upon cooling to room temperature. The magnitude of ΔH for the transition upon heating to 100° C. is markedly larger for rFSH than hCG, while the magnitude of ΔH for the transition in a concomitant scan (i.e. heating the sample to 100° C., cooling to 25° C. and performing a second scan to 100° C.) is in the same size range for rFSH and hCG.

Effect of Addition of Sugar or Salt on hCG and rFSH Tm

Addition of salt to aqueous protein solutions is expected to influence the stability of the protein in solution and hence affect the protein denaturation temperature.

Figure 5:
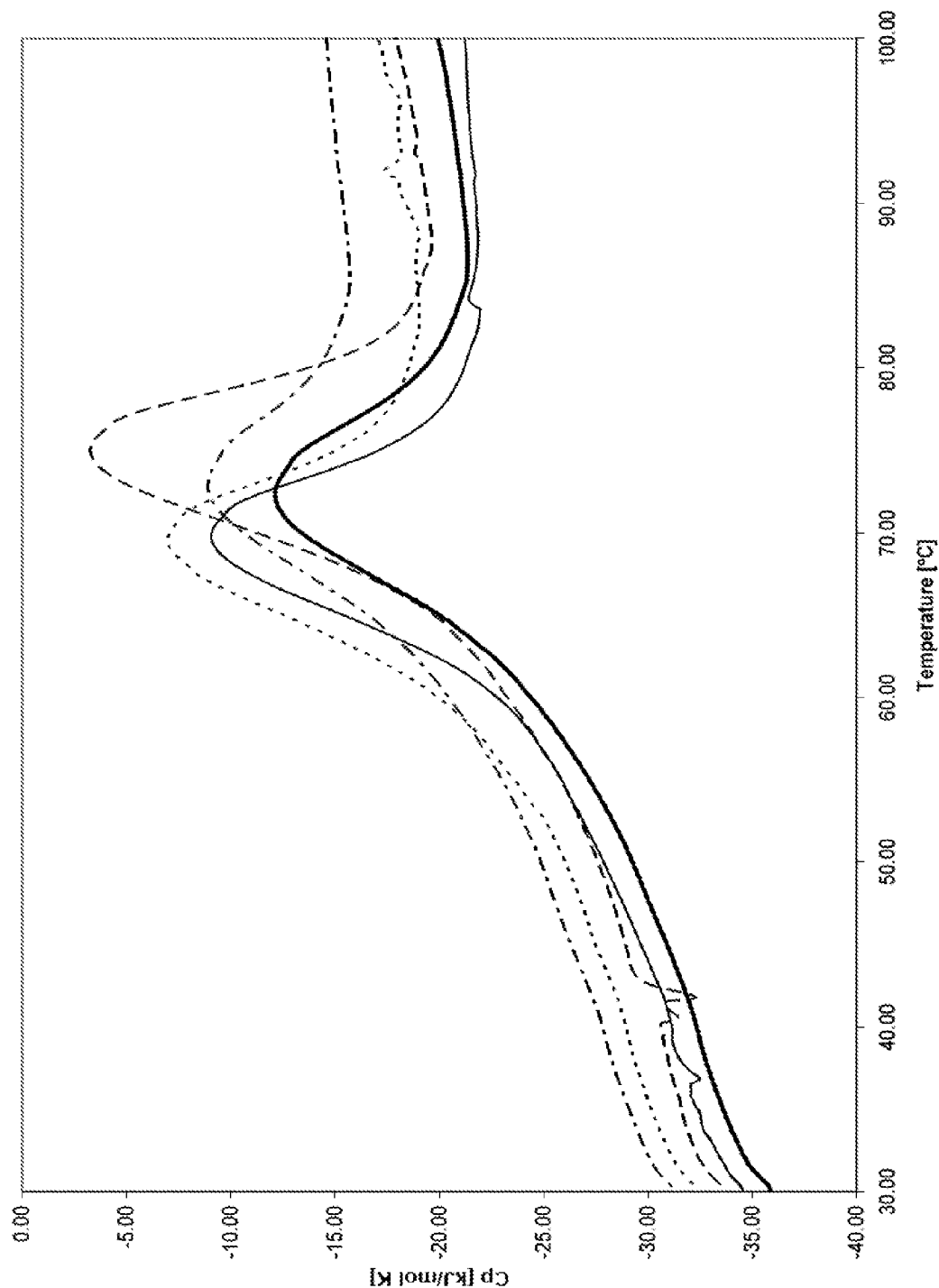
Figure 6:
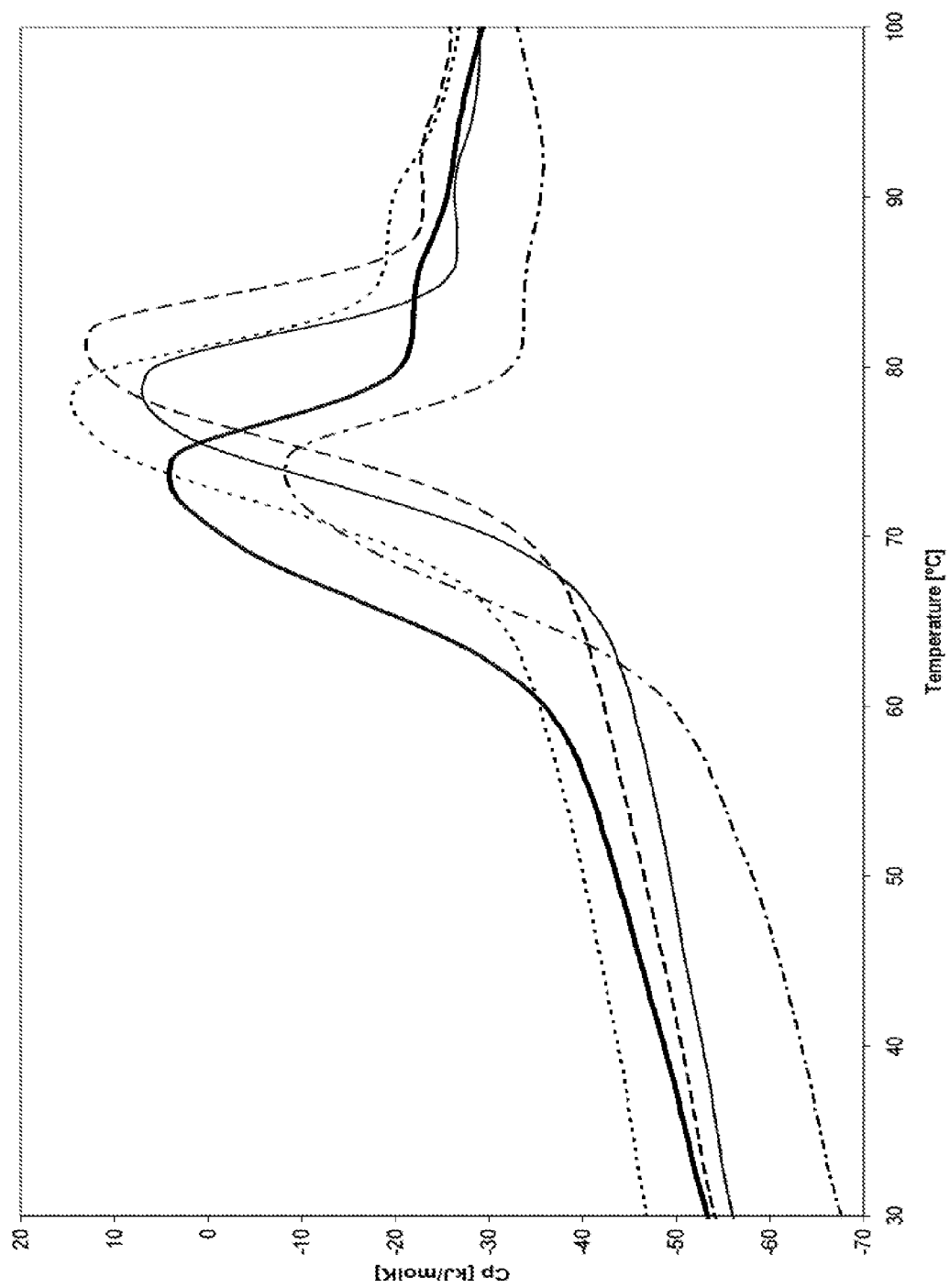

When measuring the effect of various sodium salts on hCG and rFSH Tm quite surprisingly, the stabilising/destabilising effect expected according to the Hofmeister series is not observed when varying the anions, see FIG. 5, FIG. 6 and Table 27. For hCG both sodium sulphate and sodium chloride is actually destabilising the protein, while for rFSH these salts stabilise the protein. For both hCG and rFSH sodium perchlorate, which is expected to have a destabilising effect on proteins actually increased Tm most of all tested sugars and salts.

TABLE 27

Denaturation temperature, Tm, and change in denaturation temperature, ΔTm (sugar/salt), for hCG samples containing 5 mg/ml hCG, 0.5 mg/ml L-methionine, 0.005 mg/ml Polysorbate 20, 1 mM sodium phosphate buffer pH 6.5 upon addition of 0.1M sugar or salt and rFSH samples containing 2.4 mg/ml rFSH, 0.5 mg/ml L-methionine, 0.005 mg/ml Polysorbate 20, 1 mM sodium phosphate buffer pH 6.5 upon addition of 0.1M sugar or salt. ΔTm (sugar/salt) = Tm$_{(sugar/salt)}$ − Tm$_{(no\ sugar/salt)}$.

| | hCG | | rFSH | |
|---|---|---|---|---|
| Sugar/salt | T$_m$ | ΔT$_m$ | T$_m$ | ΔT$_m$ |
| No sugar or salt | 72.1° C. | — | 72.9° C. | — |
| Na$_2$SO$_4$ | 69.8° C. | −2.3° C. | 78.0° C. | 5.1° C. |
| NaCl | 69.3° C. | −2.7° C. | 77.7° C. | 4.8° C. |
| NaClO$_4$ | 75.0° C. | 2.9° C. | 80.9° C. | 8.0° C. |
| Sucrose | 72.4° C. | 0.3° C. | 73.3° C. | 0.4° C. |

Effect of Addition of Sugar or Salt on hCG and rFSH Purity

Dissociation of rFSH Subunits, rFSH Purity During Storage

Since rFSH looses its bioactivity upon dissociation of the non-covalently coupled monomers, a straightforward way to follow loss of rFSH activity due to monomer dissociation is to measure the amount of rFSH LMW forms in solution. This information can be retrieved from SEC chromatography, where LMW forms eluting after the rFSH main peak is known to originate from dissociated rFSH.

In the studied formulation, no other protein related compounds, such as rFSH aggregates are observed. Hence, the rFSH protein purity can be calculated as Purity(%)=100%−LMW forms(%)     (4)

TABLE 28

The rFSH purity (%) as determined by SEC after storage at 30 ± 2° C./65 ± 5% RH.

| | | Storage time (months) | | | | |
|---|---|---|---|---|---|---|
| Sugar/salt | Preservative | 0 | 1 | 3 | 6 | 12 |
| 15 mg/ml Na$_2$SO$_4$ | — | 98.5% | 97.5% | 98.3% | 97.7% | 97.0% |
| 14 mg/ml Na$_2$SO$_4$ | 5 mg/ml Phenol | 98.3% | 96.5% | 96.9% | 96.1% | 93.5% |
| 7 mg/ml NaCl | 5 mg/ml Phenol | 98.2% | 98.3% | 96.9% | 96.9% | 95.6% |
| 75 mg/ml Sucrose | 5 mg/ml Phenol | 98.1% | 93.8% | 92.7% | 89.9% | — |
| — | 5 mg/ml Phenol | 98.0% | 92.3% | 83.1% | 76.6% | 67.8% |

As can be seen in Table 28, freshly prepared rFSH solutions containing different sugar or salts, with and without added preservative reveal similar purity, that is, similar relative amounts of dissociated rFSH (LMW forms).

Already after one month storage at 30° C., the rFSH purity decreases for samples containing phenol together with sucrose or no sugar or salt, whereas samples containing phenol and sodium sulphate or sodium chloride along with samples without added phenol did not display any significant decrease in rFSH purity (see Table 28). After six months storage at 30° C., the rFSH samples containing phenol without added sugar or salt yield an rFSH purity of less than 80%. The rFSH samples containing phenol having sucrose as stabiliser also display a marked decrease in rFSH purity, whereas samples containing phenol stabilised with either sodium chloride or sodium sulphate only display a minute decrease in rFSH purity (see Table 28). Samples not containing any preservative are most stable towards dissociation during storage, i.e. they display the highest purity, however, for an aqueous multidose formulation aimed for parenteral use, addition of a preservative is required.

Purity of hCG During Storage

Previously published data on changes in hCG purity upon storage are used as comparison to the above presented rFSH stability data (Samaritani, supra).

Already after one month storage at 50° C., the hCG purity decreases markedly. The decrease is significantly higher for samples containing sodium chloride than for samples containing sucrose (see Table 29). After six weeks storage at 50° C., the hCG purity of samples containing sodium chloride is more than 10% lower than for samples containing sucrose.

TABLE 29

The hCG purity (%) as determined by SEC after storage at 50° C. The full description of the formulations is listed on page 11 in patent EP 0814841.

| | | Storage time (weeks) | | | |
|---|---|---|---|---|---|
| Sugar/salt | Preservative | 0 | 1 | 2 | 6 |
| 7 mg/ml NaCl | 5 mg/ml Phenol | 100% | 89.7% | 85.6% | 71.7% |
| 75 mg/ml Sucrose | 5 mg/ml Phenol | 100% | 94.1% | 90.3% | 83.0% |

Comparison of hCG and rFSH $T_M$ and Purity

As can be seen in Table 30, both the rFSH and hCG denaturation temperature obtained by DSC correlates well with the rFSH and hCG purity as obtained from real time stability data. Similar correlation between DSC and real time stability as analysed by SEC has been presented previously for recombinant antibodies and recombinant glycoproteins.

Real time stability data for rFSH is determined at 30° C. Since the rFSH product is aimed for refrigerated long term storage, 25-30° C. is a suitable range for accelerated stability studies. Real time stability data for hCG is only available for up to 12 weeks storage at 50° C., 11 weeks storage at 25° C. and 40° C. and 6 weeks storage at 50° C. 5 For temperatures of 40° C. or lower, the decrease in hCG purity is less than 6% during storage both for formulations with sucrose and sodium chloride and therefore it is hard to differentiate between the effect of various sugar and salts already after 11-12 weeks storage. Only at 50° C., the various formulations can be differentiated clearly, albeit the trend observed at lower temperatures are the same as at 50° C.

TABLE 30

The purity as determined by SEC and the denaturation temperature as determined with DSC for hCG and rFSH. The purity for hCG is determined after 6 weeks storage at 50° C. and the purity for rFSH is determined after 6 months storage at 30° C.

| | hCG | | rFSH | |
|---|---|---|---|---|
| Sugar/salt | Purity* | $\Delta T_m$** | Purity# | $\Delta T_m$## |
| Na$_2$SO$_4$ | — | -2.3° C. | 96.1% | 5.1° C. |
| NaCl | 71.7% | -2.7° C. | 96.9% | 4.8° C. |
| Sucrose | 83.0% | 0.3° C. | 89.9% | 0.4° C. |

*Samples containing 10000 IU/ml hCG, 154 mM NaCl or 300 mM sucrose, 10 mM phosphate buffer pH 7.
**Samples containing 5 mg/ml (35 300 IU/ml) hCG, 0.1M sugar or salt, 0.5 mg/ml L-methionine, 0.005 mg/ml Polysorbate 20, 1 mM sodium phosphate buffer pH 6.5.
Samples containing 600 IU/ml rFSH, 43 mM Na$_2$SO$_4$ or 120 mM NaCl or 219 mM sucrose, 1.0 mg/ml L methionine, 0.005 mg/ml Polysorbate 20, 5 mg/ml phenol, 1 mM sodium phosphate buffer pH 6.5.
Samples containing 2.4 mg/ml (36 300 IU/ml) rFSH, 0.1M sugar or salt, 0.5 mg/ml L-methionine, 0.005 mg/ml Polysorbate 20, 1 mM sodium phosphate buffer pH 6.5.

CONCLUSIONS

Studies of the hCG and rFSH stability in various solutions by means of hCG and rFSH denaturation temperatures as well as hCG and rFSH purities after storage at elevated temperatures yield unambiguous evidence for the influence of different sugars and salts on the hCG and rFSH stability in solution. The two techniques used, liquid DSC and SEC chromatography, both display concordant results. These results have been clearly confirmed by the present real-time stability data.

Studies of the rFSH stability in various solutions by means of changes in rFSH secondary structure (by CD spectroscopy—Example 1), rFSH denaturation temperature (changes in tertiary and quaternary structure by DSC—Example 2) or the relative amount of dissociated rFSH formed after storage at 30±2° C./65±5% RH (changes in quaternary structure by SEC—Example 3) yield unambiguous evidence for the influence of preservatives and stabilisers on the rFSH stability in solution. The three techniques used, CD, DSC and SEC chromatography all display concordant results.

Concluding the results from all of Examples 1-3, it is clearly seen that the addition of a preservative, phenol or benzyl alcohol, decreases the rFSH stability in solution. Other phenolic preservatives, like m-cresol and chlorocresol are expected to give rise to similar destabilising effects. The destabilising effect observed for rFSH upon addition of preservative corresponds well to state of the art knowledge within the area.

The addition of a pharmaceutically acceptable alkali metal Na$^+$ or K$^+$-salt to rFSH solutions neutralises the destabilising effect of preservatives on rFSH and—most advantageously—increases the stability of rFSH in solution as compared with rFSH solutions containing neither a preservative nor a salt. All tested sodium and potassium salts give rise to increased rFSH stability independent of the anions used; e.g inorganic anions like sulphate, chloride and perchlorate and also using organic anions like citrate, acetate and tartrate. Varying the cation of the salts yields a large impact on the degree of rFSH stabilisation; monovalent cations, specifically salts with the cations sodium or potassium give rise to a pronounced stabilising effect on rFSH. The addition of sodium perchlorate to an rFSH solution gives rise to the most stable rFSH solutions, however, perchlorates are generally highly reactive and oxidising agents and perchlorates are therefore not approved as inactive ingredients in pharmaceutical formulations. Hence, sodium salts or potassium salts of sulphate and chloride, are the most favourable stabilising agents.

Addition of sucrose to hCG or rFSH solutions yield a slight increase in protein stability, both for hCG and rFSH, while the addition of sodium chloride has a destabilising effect on hCG and a stabilising effect on rFSH (see example 4). Addition of sodium perchlorate to hCG and rFSH solutions has a stabilising effect on both hCG and rFSH (example 4). The stabilizing effect of these salts on rFSH solutions is surprisingly clearly better than the stabilizing effect observed for sucrose.

The conclusions of these results are the following:
1) under the studied conditions, the salt effects on hCG and rFSH stability does not follow the Hoffmeister series
2) despite the fact that hCG and FSH are structurally very similar (i.e. they belong to the same class of proteins, they are both glycosylated and they both consist of two subunits whereof the α-subunit is identical in the two proteins), the effect of various sugar and salts like sucrose and sodium chloride on the protein stability is different for hCG and rFSH. Very surprisingly, for the very similar proteins like hCG and rFSH, salts do not display the same stabilising effect.

3) Na$^+$- and K$^+$-salts display their stabilizing effect on FSH solutions, independent of the anions used.

4) the stabilizing effect of Na$^+$- and K$^+$-salts on FSH solutions can counteract the de-stabilizing effect of preservatives.

ABBREVIATIONS AND DEFINITIONS

The following abbreviations and definitions are used throughout the text and Examples:
ΔT$_m$ Change in denaturation temperature upon addition of a preservative or salt, see further T$_m$
ARTs Assisted reproductive technologies
BA benzyl alcohol
BTG Bio-Technology General
CD Circular Dichroism
CHO Chinese hamster ovary
CoA Certificate of Analysis
DNA Deoxyribonucleic acid
DSC Differential Scanning Calorimetry
FSD Female Sexual Dysfunction
FSH Follicle Stimulating Hormone
hCG Human Chorionic Gonadotropin
IU International Units
    A measure of the rFSH bio activity as determined by a Steelman-Pohley Bioassay according to Ph. Eur. and USP.
IUI Intrauterine insemination
LC-UV Liquid Chromatography with Ultra Violet detection
LH Luteinising Hormone
LMW Low Molecular Weight form, consist mainly or solely of dissociated monomeric protein.
OI Ovolation induction
p.a. Pro Analysis
Ph. Eur. European Pharmacopoeia
RH Relative Humidity
rFSH Recombinant human Follicle Stimulating Hormone
SEC Size Exclusion Chromatography
SRCD Synchrotron Radiation Circular Dichroism
T$_m$ Midpoint of the thermal transition or Transition midpoint or Denaturation temperature
    The temperature when half of the protein molecules are folded and half of the protein molecules are unfolded.
TRIS 2-Amino-2-hydroxymethyl-propane-1,3-diol
TSH Thyroid Stimulating Hormone
USP United States Pharmacopoeia
UV Ultra Violet

The invention claimed is:

1. A liquid formulation comprising:
follicle stimulating hormone (FSH); and
sodium sulfate in an amount that stabilizes the FSH.

2. The liquid formulation of claim 1, wherein the formulation comprises sodium chloride in addition to the sodium sulfate.

3. The liquid formulation of claim 1, wherein the sodium sulfate is present in the formulation in an amount in the range from 20 to 500 mM.

4. The liquid formulation of claim 1, wherein the FSH is recombinant FSH.

5. The liquid formulation of claim 1, wherein the formulation is injectable.

6. A method for stabilization of a liquid FSH formulation, which comprises preparing a liquid formulation comprising follicle stimulating hormone (FSH) and sodium sulfate in an amount that stabilizes the FSH.

7. The method of claim 6, wherein the formulation further comprises sodium chloride.

8. The composition of claim 1, wherein the sodium sulfate is present in the formulation at a concentration in the range from 30-300 mM.

9. The composition of claim 6, wherein the sodium sulfate is present in the formulation at a concentration in the range from 50-200 mM.

10. The method of claim 6, wherein the sodium sulfate is present in the formulation at a concentration in the range from 30-300 mM.

11. The method of claim 6, wherein the sodium sulfate is present in the formulation at a concentration in the range from 50-200 mM.

12. A liquid FSH formulation comprising:
follicle stimulating hormone (FSH) at a concentration in the range from about 50 IU/mL to about 800 IU/mL;
sodium sulfate at a concentration in the range from about 1 mg/mL to about 100 mg/mL;
polysorbate 20 at a concentration in the range from about 0.001 to about 0.05 mg/mL;
L-methionine at a concentration in the range from about 0.1 to about 10 mg/mL; and
sodium phosphate buffer at a concentration in the range from about 0.1 mM to about 10 mM and a pH in the range from about 6 to about 8.

13. A liquid FSH formulation according to claim 12, wherein the FSH is at a concentration of about 600 IU/mL.

14. A liquid FSH formulation according to claim 12, wherein the liquid formulation has an osmolality of about 300 mOsmol/kg.

15. A liquid FSH formulation according to claim 12 comprising:
FSH at a concentration of in the range from about 100 IU/mL to about 600 IU/mL;
sodium sulfate at a concentration of about 14 mg/mL;
polysorbate 20 at a concentration of about 0.005 mg/mL;
L-methionine at a concentration of about 1 mg/mL; and
sodium phosphate buffer at a concentration of about 1 mM and a pH of about 6.5.

16. A liquid FSH formulation according to claim 15, wherein the liquid formulation has an osmolality of about 300 mOsmol/kg.

17. A liquid FSH formulation according to claim 15, wherein the FSH is at a concentration of about 600 IU/mL.

18. A liquid FSH formulation according to claim 15, wherein the liquid formulation has an osmolality of about 300 mOsmol/kg.

19. A liquid FSH formulation according to claim 12, wherein the FSH is at a concentration in the range from about 100 IU/mL to about 600 IU/mL.

20. A liquid FSH formulation comprising:
follicle stimulating hormone (FSH) at a concentration in the range from about 50 IU/mL to about 800 IU/mL; and
sodium sulfate at a concentration in the range from about-1 mg/mL to about 100 mg/mL.

21. A liquid FSH formulation according to claim 20, wherein the FSH is at a concentration in the range from about 100 to about 600 IU/mL.

22. A liquid FSH formulation according to claim 20, wherein the FSH is at a concentration of about 600 IU/mL.

23. A liquid FSH formulation according to claim 20, comprising sodium phosphate buffer at a concentration in the range from about 0.1 mM to about 10 mM and a pH in the range from about 6 to about 8.

24. A liquid FSH formulation according to claim 20, comprising:
   FSH at a concentration in the range from about 100 to about 600 IU/mL;
   sodium sulfate at a concentration in the range from about-1 mg/mL to about 100 mg/mL; and
   sodium phosphate buffer at a concentration in the range from about 0.1 mM to about 10 mM and a pH in the range from about 6 to about 8.

25. A liquid FSH formulation according to claim 24, wherein the FSH is at a concentration of about 600 IU/mL.

\* \* \* \* \*